United States Patent [19]

Theissen

[11] Patent Number: 4,517,010

[45] Date of Patent: May 14, 1985

[54] 2-NITRO-5(SUBSTITUTED-PHENOXY) BENZOYL DERIVATIVES AS HERBICIDES

[75] Inventor: Robert J. Theissen, Bridgewater, N.J.

[73] Assignee: Rhone-Poulenc Inc., Monmouth Junction, N.J.

[21] Appl. No.: 485,265

[22] Filed: Apr. 15, 1983

Related U.S. Application Data

[60] Division of Ser. No. 282,316, Jul. 10, 1981, , which is a continuation-in-part of Ser. No. 117,732, Feb. 1, 1980, abandoned.

[51] Int. Cl.$^3$ ............... A01N 43/40; A01N 43/28; C07D 339/04; C07D 213/64
[52] U.S. Cl. ............................ 71/90; 71/92; 71/93; 71/94; 544/218; 544/216; 544/239; 546/302; 546/298; 548/127; 549/36; 549/37; 549/65
[58] Field of Search ............... 546/302, 298; 548/127; 544/239, 218, 216; 549/36, 65, 37; 71/92, 93, 94, 90

[56] References Cited

U.S. PATENT DOCUMENTS

| | | | |
|---|---|---|---|
| 2,841,482 | 7/1958 | Swezey et al. | 71/122 |
| 3,130,037 | 4/1964 | Scherer et al. | 71/106 |
| 3,198,824 | 8/1965 | van den Bogaart | 260/463 |
| 3,784,635 | 1/1974 | Theissen | 560/21 |
| 3,928,416 | 12/1975 | Bayer et al. | 560/21 |
| 3,950,265 | 4/1976 | Albrecht et al. | 252/311 |
| 4,048,217 | 9/1977 | Rohr | 560/20 |
| 4,063,929 | 12/1977 | Bayer et al. | 71/115 |
| 4,209,318 | 6/1980 | Johnson | 71/88 |
| 4,221,581 | 9/1980 | Rohr et al. | 71/70 |
| 4,259,510 | 3/1981 | Johnson | 560/21 |
| 4,270,948 | 6/1981 | Takahashi et al. | 71/100 |

*Primary Examiner*—Alan L. Rotman
*Attorney, Agent, or Firm*—Morgan, Finnegan, Pine, Foley & Lee

[57] ABSTRACT

There is provided a new class of derivatives of 2-nitro-5-(substituted-phenoxy) benzoyl compounds that have pre- and post-emergence herbicidal activity. The derivatives include certain substituted phenyl esters, phenyl thioesters; heterocyclic esters; substituted alkyl and alkylthio esters; carbonates and thiocarbonates; benzoyl phosphonates; substituted alkanones and substituted amides.

20 Claims, No Drawings

2-NITRO-5(SUBSTITUTED-PHENOXY) BENZOYL DERIVATIVES AS HERBICIDES

CROSS-REFERENCES TO RELATED APPLICATIONS

This is a division of application Ser. No. 282,316 filed July 10, 1981, which is a continuation-in-part application No. Ser. No. 117,732 filed Feb. 1, 1980, now abandoned.

Applicant Theissen herein has been granted a series of patents relating to 2-nitro-5-(substituted-phenoxy) benzoic acid derivatives including the salt, alkyl and cycloalkyl esters, alkylthio esters, phenyl ester, alkyl and dialkyl amido and benzoyl chloride forms. Illustrative of those patents are U.S. Pat. Nos. 3,652,645; 3,784,635; 3,873,302; 3,983,168 and 3,907,866.

BRIEF SUMMARY OF THE INVENTION

This invention provides certain herbicidal compounds falling within the general formula:

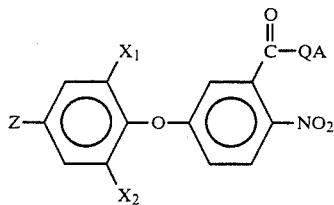

wherein $X_1$ is halogen, $X_2$ is selected from halogen and hydrogen, and Z is a polyhalo$_{1-9}$ alkyl$_{1-4}$ group such as $CF_3$, $CHF_2$, $C_4F_9$, $CF_2CH_2CH_3$ and $CH_2Cl$. Preferably, $X_1$ is chloro, Z is $CF_3$ and $X_2$ is hydrogen. QA in the formula includes certain groups more fully described below.

DETAILED DESCRIPTION

The specific 2-nitro-5-(substituted-phenoxy) benzoyl compounds are described below. One method for preparing these compounds is the use of the Ullman ether synthesis reaction between the alkali metal (e.g., Na, K) salt of a suitable substituted phenol, e.g., m-hydroxy benzoic acid or m-cresol with an active halogen-substituted aromatic, e.g., 3,4-dichlorobenzotrifluoride. The intermediate obtained may be nitrated and subsequently derivatized by known procedures to the desired benzoyl compound. Where m-cresol is used as a starting material, the product obtained can be oxidized and subsequently nitrated before the aforementioned derivatization.

A. Substituted phenyl esters, phenylthio ester, substituted phenylthio esters

Illustrative compounds of this class are those of the formula:

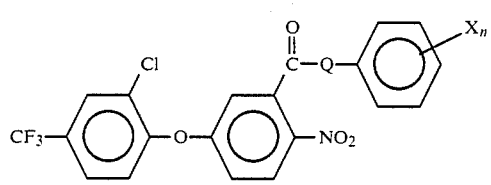

where

Q is O or S, n is an integer from 1 to 5, and

X is selected from $NO_2$; lower alkyl of $C_{1-4}$; halogen; phenyl; COOR where R is lower alkyl of $C_{1-4}$, H or a cation selected from alkali metals, alkaline earth metals, ammonium and lower alkyl and di-lower alkyl ammonium; CN; lower alkyl thio of $C_{1-4}$; lower alkoxy of $C_{1-4}$; trifluoromethyl; and combinations thereof. X can be hydrogen when Q is sulfur.

Compound 1

Preparation of 2,4-dinitro-6-sec-butylphenyl 5-[-2-chloro-4-(trifluoromethyl)phenoxy]-2-nitrobenzoate.

To a stirred solution of 2,4-dinitro-6-sec-butylphenol (3.60 g, 0.015 mole) and 5-[-2-chloro-4-(trifluoromethyl)phenoxy]-2-nitrobenzoyl chloride (5.68 g, 0.015 mole) in toluene (25 ml) was added triethylamine (1.50 g, 0.015 mole). The temperature exothermed to 45° C. and there was an immediate precipitation of triethylamine hydrochloride. The reaction was stirred and heated to 110° F. for 15 hours. The precipitate was filtered from the cooled solution, washed and dried to give triethylamine hydrochloride (1.8 g). The toluene solution was washed with 10% sodium hydroxide (3×25 ml). The toluene was then stripped off on a rotary evaporator to give 5.5 g (62%) of a crude brown oil which slowly crystallized. Recrystallization from methanol gave 2.1 g of an off white solid, mp. 109°-110° C.

I.R. (nujol): C=O, 1765 cm$^{-1}$

NMR (D6 Acetone): triplet 0.9 ppm (3H, J=7.0 Hz): doublet 1.37 ppm (3H, J=7.0 Hz): multiplet 1.82 ppm (2H); multiplet 3.35 ppm (1H); multiplet 7.5-8.2 (5H); doublet 8.45 ppm (1H, J=9.0 Hz); doublet 8.82 ppm (1H, J=2.4 Hz); doublet 9.02 ppm (1H, J=2.4 Hz).

In a similar manner the following compounds were prepared as defined according to Formula II:

| Compound | Q (O or S) | Phenyl Substitution $X_n$ | m.p., °C. |
|---|---|---|---|
| 2 | O | 2-$NO_2$ | 137-9 |
| 3 | O | 3-$NO_2$ | 93.5 |
| 4 | O | 4-$NO_2$ | 115-7 |
| 5 | O | 5-$CH_3$—2$NO_2$ | 88-90 |
| 6 | O | 2-Cl—4$NO_2$ | 99-101 |
| 7 | O | 4-Cl | 135-7 |
| 8 | O | 4-Cl—2-$CH_3$ | 121-2 |
| 9 | O | 2-Cl—4-$CH_3$ | 105-7 |
| 10 | O | 2-Cl—4-phenyl | 128-30 |
| 11 | O | 2,4-(Cl)$_2$ | 144-7 |
| 12 | O | 4-$COOCH_3$ | 103-6 |
| 13 | O | 4-CN | 103-5 |
| 14 | O | 4-$SCH_3$ | 94-5 |
| 15 | O | 3-$OCH_3$ | 95-7 |
| 16 | O | 4-$OCH_3$ | 128-9 |
| 17 | O | 3-$CF_3$ | oil |
| 18 | O | 4-COONa | 215-20 |
| 19 | O | 4-COOH | 191-8 |
| 20 | S | H | oil |
| 21 | S | 4-Cl | 128-30 |
| 22 | S | 4-$CH_3$ | 90-3 |
| 23 | S | 4-$OCH_3$ | oil |
| 24 | S | 3,4-(Cl)$_2$ | oil |

Other compounds of this class include:

| Compound | |
|---|---|
| 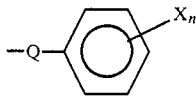 | 2,6-diethylphenyl 5-[2-chloro-4-(trifluoromethyl) phenyoxy]-2-nitrobenzoate |
| 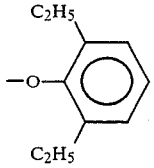 | S—[2-carboxyphenyl) 5-[2-chloro-4-(trifluoromethyl) phenoxy]-2-nitrobenzenecarbothioate |
| 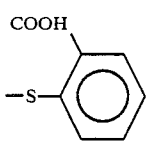 | 4-cyano-2,6-dibromophenyl 5-[2-chloro-4-(trifluoromethyl) phenoxy]-2-nitrobenzoate |
| 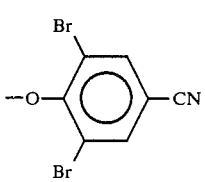 | 3,6-dichloro-2-methoxycarbonylphenyl 5-[2-chloro-4-(trifluoromethyl) phenoxy]-2-nitrobenzoate |
| 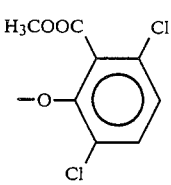 | (2,6-di-6-butyl) phenyl 5-[2-chloro-4-(trifluoromethyl) phenoxy]-2-nitrobenzoate |
| 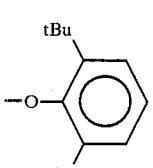 | pentachlorophenyl 5-[2-chloro-4-(trifluoromethyl) phenoxy]-2-nitrobenzoate |

B. Heterocyclic Esters

Illustrative compounds of this class are those of the formula:

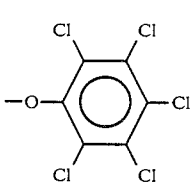

where Q is O or S and Het is a substituted or unsubstituted heterocyclic ring of 5 to 7 members comprising carbon in combination with one or more of sulfur, oxygen and nitrogen where a carbon atom on the ring is bound directly to Q.

Compound 25

Preparation of 3-pyridyl 5-[2-chloro-4-(trifluoromethyl)phenoxy]-2-nitrobenzoate: To a stirred solution of 5-[2-chloro-4-(trifluoromethyl)phenoxy]-2-nitrobenzoyl chloride (3.79 g, 0.01 mole) and triethyl amine (1.01 g, 0.01 mole) in toluene (50 ml) was added 3-hydroxypyridine (0.95 g, 0.01 mole). The temperature exothermed to 33° C. and there was an immediate precipitate. The reaction was then refluxed for 24 hours, cooled to room temperature and the triethylamine hydrochloride precipitate collected by filtration. The toluene solution was washed with dilute sodium hydroxide solution and then with saturated sodium chloride solution. After drying and evaporation of the solvent there was obtained 3.1 g of brown oil which solidified. This was triturated with hexane and the solid filtered and dried to give a tan product, m.p. 65°–68° C.

I.R. (nujol): C=O, 1765 $cm^{-1}$

NMR($D_6$-acetone): complex multiplet 7.2–8.1 ppm (7H); doublet 8.50 ppm (1H, J=4.5 Hz); multiplet 8.75 ppm (2H).

Compound 26

This compound is defined in accordance with Formula III as "Q" is O and "Het" is

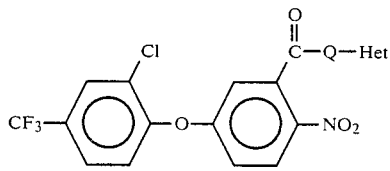

The compound was prepared by the procedure shown for Compound 25. Compound 26 has an m.p. of 153°–161° C.

Other compounds of this class include:

| —Q—Het | Compound Name |
|---|---|
| 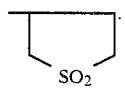 | 3-(1,2,5 thiadiazoloyl)-5-[2-chloro-4-trifluoromethyl) phenoxy]-2-nitrobenzoate |
| 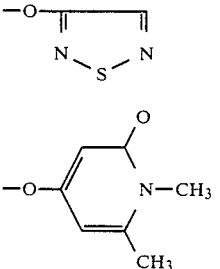 | 1,2-dihydro-1,6-dimethyl-2-oxo 4-pyridinyl 5-[2-chloro-4-(trifluoromethyl) phenoxy]-2-nitrobenzoate |
| 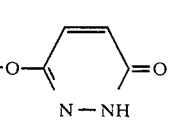 | 6(2,3-dihydro-3-oxo-pyridazinyl) 5-[2-chloro-4-(trifluoromethyl) phenoxy]-2-nitrobenzoate |
| 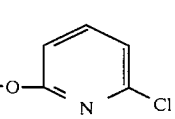 | 2-chloro-6-pyridinyl 5-[2-chloro-4-(trifluoromethyl) phenoxy]-2-nitrobenzoate |
| 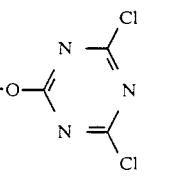 | s-(2,6-dichloro-4-s-triazinyl) 5-[2-chloro-4-(trifluoromethyl) phenoxy]-2-nitrobenzoate |

| —Q—Het | Compound Name |
|---|---|
| (N—N thiadiazole with S, CH3) —S— | S—(2-methyl 1,3,4,-thiadiazol-5-yl) 5-[2-chloro-4-trifluoromethyl) phenoxy]-2-nitrobenzene-carbothioate |
| —S— (pyridinyl N-oxide) | S—(2-pyridinyl) 5-[-2-chloro-4-(trifluoromethyl) phenoxy]-2-nitrobenzenecarbothioate N—oxide |
| —S— (4-methyl-3-thioxo-1,2-dithiol-5-yl) | S—[4-methyl-3-thioxo-3H—1,2-dithiol-5-yl] 5-[2-chloro-4-(trifluoromethyl) phenoxy]-2-nitrobenzene-carbothioate |
| —S—C(=N—CN(Et)2)—N=CN(Et)2 triazinyl | S—[3,5-bis-(diethylamino)-s-triazinyl] 5-[2-chloro-4-(trifluoromethyl) phenoxy]-2-nitrobenzene-carbothioate |

Substituted C$_{1-4}$ Alkyl Esters

Illustrative compounds of this class are those of the formula:

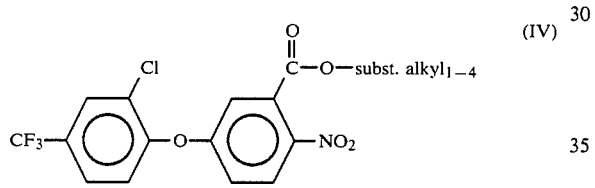

(IV)

wherein the substituents on the straight or branched C$_{1-4}$ alkyl group are selected from cyano; phenyl;

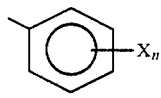

where n is 1 to 5 and X is selected from NO$_2$, lower alkyl or C$_{1-4}$, halogen, phenyl, CN, lower alkyl thio of C$_{1-4}$, lower alkoxy of C$_{1-4}$, trifluoromethyl and combinations thereof;

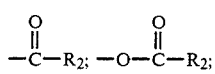

phenoxy; nitro; SR$_1$; SOR$_1$; SO$_2$R$_1$; where R$_1$ is an alkyl of 1 to 3 carbons and R$_2$ is an alkyl or alkenyl of up to 3 carbons and wherein one or more of said substituents can be attached to any one or more of the carbons on said straight or branched C$_{1-4}$ alkyl group.

The compounds of this class may be prepared by the methods shown above or alternatively by displacement of an active halogen (e.g., Haloalkyl X) with the salt of an acid (e.g.,

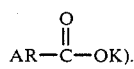

).

The following substituted C$_{1-4}$ alkyl esters as defined by Formula IV were prepared:

| Compound | Substituted Alkyl Group | m.p. °C. |
|---|---|---|
| 27 | —C(CH$_3$)$_2$CN | oil |
| 28 | —CH(CH$_3$)CN | oil |
| 29 | —CH$_2$COCH$_3$ | 83–5 |
| 30 | —CH$_2$—(phenyl) | oil |
| 31 | —CH$_2$—(phenyl-O-phenyl) | oil |
| 32 | —CH$_2$—CH$_2$—O—C(=O)—CH=CH$_2$ | oil |
| 33 | —CH$_2$—CH$_2$—O—C(=O)—C(CH$_3$)=CH$_2$ | oil |
| 34 | —CH$_2$—CH$_2$—CN | oil |
| 35 | | |
| 36 | —CH$_2$—CH$_2$—O—(phenyl) | 86–8 |
| 37 | —CH$_2$—CH$_2$—(phenyl) | 112–3 |
| 38 | —CH$_2$C(CH$_3$)$_2$—NO$_2$ | oily semisolid |
| 39 | —CH$_2$—CH$_2$—SCH$_3$ | oil |
| 40 | —CH$_2$—CH$_2$—SO$_2$CH$_3$ | 97–9 |

Other compounds of this class include:

| Substituted alkyl | Compound Name |
|---|---|
| CH$_2$—S—CH$_2$CH$_3$ | (ethylthio)methyl 5-[2-chloro-4-(trifluoromethyl) phenoxy]-2-nitro-benzoate |
| CH$_2$S(=O)—CH$_2$CH$_3$ | (ethylsulfinyl)methyl 5-[2-chloro-4-(trifluoromethyl) phenoxy]-2-nitro-benzoate |
| CH$_2$S(=O)—CH$_2$CH$_3$ | (ethylsulfinyl)methyl 5-[2-chloro-4-(trifluoromethyl) phenoxy]-2-nitrobenzoate |
| CH(CH$_3$)—C(=O)CH$_3$ | 1-acetylethyl 5-[2-chloro-4-trifluoromethyl) phenoxy]-2-nitrobenzoate |
| CH$_2$CH$_2$CH$_2$C(=O)CH$_3$ | 3-acetylpropyl 5-[2-chloro-4-(trifluoromethyl) phenoxy]-2-nitrobenzoate |
| CH$_2$CH$_2$SCH$_3$ | 2-(methylsulfinyl) ethyl 5-[2-chloro-4-(trifluoromethyl) phenoxy]-2-nitrobenzoate |

| Substituted alkyl | Compound Name |
|---|---|
| 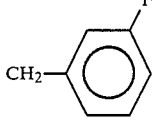 | (3-fluorophenyl) methyl 5-[2-chloro-4-(trifluoromethyl) phenoxy]-2-nitrobenzoate |

D. Carbonates and Thiocarbonates

Illustrative compounds of this class are those of the formula:

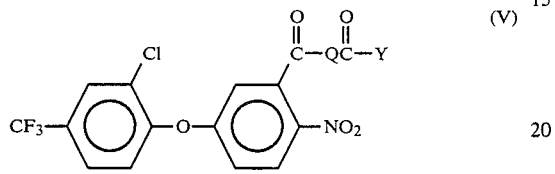 (V)

where Q is O or S and Y is a straight or branched alkoxy or alkylthio of 1 to 6 carbons, a dialkylamino of 2 to 6 carbons, or a heterocyclic amine such as morpholine.

Compound 41

Preparation of S[(ethylthio)carbonyl]5-[2-chloro-4-(trifluoromethyl)phenoxy]-2-nitrobenzoate.

To a stirred solution of 5-[2-chloro-4-(trifluoromethyl)phenoxy]-2-nitrobenzoic acid (3.0 g, 0.0083 mole) in ether (15 ml) was added triethylamine (0.84 g, 0.0083 mole). A precipitate formed. The reaction was cooled to 4° C. and a solution of ethylchlorothioformate (1.03 g, 0.0083 mole) in ether was added dropwise. Cooling was maintained during initial exotherm. The reaction was then stirred at room temperature for twenty hours. The precipitate of triethyl amine hydrochloride was filtered. The ether was washed consecutively with 10% hydrochloric acid solution, 5% sodium hydroxide solution and water. The dried solution was evaporated to give 3.04 g of a yellow oil.

I.R. (neat): C=O, 1675 and 1800 cm$^{-1}$

NMR (CDCl$_3$): triplet 1.37 ppm (3H, J=7.0 Hz); quartet 3.12 ppm (2H, J=7.0 Hz); complex multiplet 7.0–8.0 ppm (5H); doublet 8.15 ppm (1H, J=9.6 Hz).

In a similar manner, the following compounds, as defined in accordance with Formula V, were prepared:

| Compound | Q | Y | m.p. °C. |
|---|---|---|---|
| 42 | O | OCH$_3$ | oil |
| 43 | O | OCH$_2$CH$_3$ | oil |
| 44 | O | OCH$_2$CH$_2$CH$_3$ | oily semi-solid |
| 45 | O | OCH(CH$_3$)$_2$ | oily semi-solid |
| 46 | O | OCH$_2$CH$_2$CH$_2$CH$_3$ | oil |
| 47 | O | OCH$_2$CH(CH$_3$)$_2$ | oil |
| 48 | S | OCH$_3$ | oil |
| 49 | S | 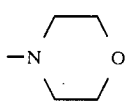 | 137–8° |

S[(propylthio)thionocarbonyl]5-[2-chloro-4-(trifluoromethyl)phenoxy]-2-nitrobenzenecarbothioate is a further illustrative compound of this class wherein Q is S and Y is —SC$_3$H$_7$.

Benzoyl Phosphonates

Illustrative compounds of this class are those of the formula:

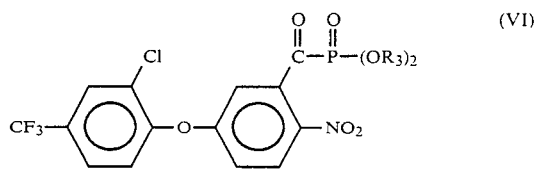 (VI)

where R$_3$ is straight or branched alkyl of 1 to 6 carbons.

Compound 50

Preparation of 5-[2-chloro-4-(trifluoromethyl)-phenoxy]-2-nitrobenzoyl-phosphonic acid, diisopropyl ester.

To a stirred solution of 5-[2-chloro-4-(trifluoromethyl)phenoxy]-2-nitrobenzoyl chloride (3.8 g, 0.01 mole) in ether (100 ml) was added triisopropyl phosphite (2.1 g, 0.01 mole). The reaction was refluxed for one hour and the disappearance of phosphite monitored by v.p.c.. The ether was stripped off and the resulting oil placed under vacuum (1.0 mm) at 40° C. for two hours. The resulting amber liquid amounted to 5.2 g.

I.R. (neat): C=O, 1692 and 1730 cm$^{-1}$

NMR (CDCl$_3$): doublet 1.29 ppm (3H, J=6.0 Hz); doublet 1.37 ppm (3H, J=6.0 Hz); multiplet 4.88 ppm (1H); complex multiplet 6.9–8.0 ppm (5H); broad doublet 8.37 ppm (1H, J=9.0 Hz).

In a similar manner, the following compound was prepared as an additional example of a benzoyl phosphonate.

Compound 51

5-[2-chloro-4-(trifluoromethyl)phenoxy]-2-nitrobenzoy-phosphonic acid diethyl ester was prepared and was an oil.

F. Substituted Alkanone Compounds

Illustrative compounds of this class are those of the formula:

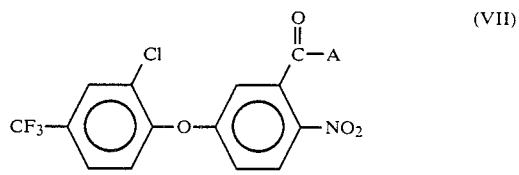 (VII)

where A is an alkyl of 1–3 carbons or hydrogen.

Compound 52

Preparation of 5-[2-chloro-4-(trifluoromethyl)-phenoxy]-2-nitrophenyl ethanone (A is —CH$_3$).

A stirred solution of 3-[2-chloro-4-(trifluromethyl)-phenoxy]phenyl ethanone (15.7 g, 0.05 mole) in dichloroethane (40 ml) was cooled to 0.5° C. Nitric acid (95%) (4.95 g, 0.075 mole) was added, followed by the dropwise addition of 95% sulfuric acid (12.3 g, 0.125 mole) while maintaining the temperature below 5°–10° C. Allowed reaction to warm to room temperature. The progress of the reaction was monitored by v.p.c. The reaction solution was poured onto ice water and the organic solution separated, washed with water and dried. The solvent was evaporated to give 16 g of a brown oil, which was extracted with hot heptane. Upon cooling, the heptane solution furnished an oil fraction which solidified to give 8.8 g of a brown solid, m.p. 58°–60° C.

I.R. (nujol mull): C=O, 1710 cm$^{-1}$; NO$_2$, 1530 and 1315 cm$^{-1}$.

Compound 53

5-[2-chloro-4-trifluoromethyl)phenoxy]-2-nitrobenzaldehyde ("A" is hydrogen in Formula VII) was prepared. It had a melting point of 99°–100° C.

G. Amides

Illustrative compounds of this class include those of the formula:

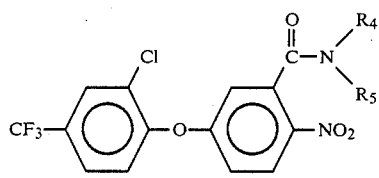

wherein
R$_4$ is selected from hydrogen and straight or branched chain alkyl of 1–4 carbon:
R$_5$ is selected from: phenyl;

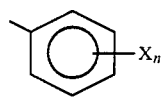

where n is 1 to 5 and X is selected from NO$_2$, lower alkyl of C$_{1-4}$, halogen, phenyl, COOR where R is lower alkyl of C$_{1-4}$ or H or a cation, CN, lower alkyl thio of C$_{1-4}$, lower alkoxy of C$_{1-4}$, trifluoromethyl and combinations thereof; heterocyclicalkyl and heterocyclic, heterocyclics of a 5 to 7 member ring comprising carbon in combination with one or more of sulfur, oxygen and nitrogen; hydroxyl; alkoxy of 1–3 carbons; —R$_6$-CO$_2$R$_6$, where R$_6$ is an alkyl or alkenyl of up to 3 carbons; —R$_6$CONH$_2$; R$_6$CON(R$_2$)$_2$; alkoxyalkyl where the alkoxy and alkyl may each contain a straight or branched C$_{1-3}$ alkyl chain; or
where R$_4$ and R$_5$ together form a heterocyclic ring as hereinabove defined.

Compound 54

Preparation of N-phenyl 5-[2-chloro-4-(trifluoromethyl)phenoxyl]-2-nitrobenzamide.

To a stirred solution of 5-[2-chloro-4-(trifluoromethyl)phenoxy]-2-nitrobenzoyl chloride (5.68 g, 0.015 mole) in toluene (35 ml) was added aniline (2.8 g, 0.30 mole). The temperature immediately rose to 45° C. The reaction was then heated to reflux for twelve hours. The cooled reaction was poured into dilute hydrochloric acid solution. The residual solids were filtered, washed with warm water and dried to give 4.1 g of a gray solid m.p. 190°–4° C. Recrystallization from methanol gave 3.8 g, m.p. 191°–4° C.

I.R. (nujol): C=O, 1660 cm$^{-1}$

NMR (D$_6$-Acetone): complex multiplet 7.0–8.1 ppm (10H); doublet 8.32 ppm (1H, J=9.0 Hz); broad singlet 9.95 ppm (1H).

In a similar manner, the following compounds were prepared:

| Compound | R$_4$ | R$_5$ | m.p. °C./oil |
|---|---|---|---|
| 55 | H | 4-Cl-phenyl | 145–8 |
| 56 | H | 3-CF$_3$-phenyl | 179–81 |
| 57 | H | 3,4-diCl-phenyl | 155–8 |
| 58 | H | 2,6-diCH$_3$-phenyl | 169–71 |
| 59 | H | 2,6-diC$_2$H$_5$-phenyl | 185–7 |
| 60 | CH(CH$_3$)$_2$ | phenyl | 144–6 |
| 61 | H | —CH$_2$-tetrahydrofuryl | 140–1 |
| 62 | H | OH | oil |
| 63 | H | OCH$_3$ | 171–4 |
| 64 | CH$_3$ | OH | oil |
| 65 | CH$_3$ | OCH$_3$ | oil |
| 66 | H | CH$_2$COOC$_2$H$_5$ | 136–7 |
| 67 | H | —CH(CH$_3$)COOC$_2$H$_5$ | oil |
| 68 | H | —CH(CH$_3$)CONH$_2$ | 160–3 |
| 69 | H | —CH$_2$CH$_2$OC$_2$H$_5$ | 86–8 |
| 70 | H | —CH$_2$CH$_2$CH$_2$OCH$_3$ | 102–4 |

-continued

| 71 | H | 158-60 |
|---|---|---|
| Compound | R₄ and R₅ | m.p. °C./oil |
| 72 | 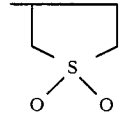 | 107-8 |
| 73 |  | 128-32 |
| 74 | 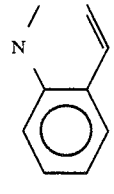 | 124-6 |
| 75 | 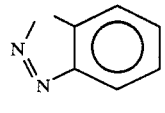 | 169-72 |
| 76 | 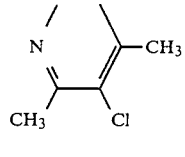 | oil |
| 77 | 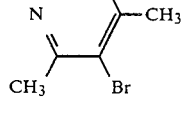 | 125-8 |

$$-N\begin{matrix}R_4\\R_5\end{matrix}$$

| | Compound Name |
|---|---|
| 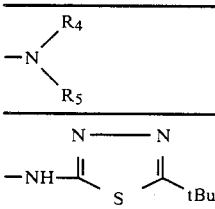 | N—[2-(5-t-butyl-1,3,4 thiadiazolyl)]5-[2-chloro-4-(trifluoromethyl)phenoxy]-2-nitrobenzamide |
| 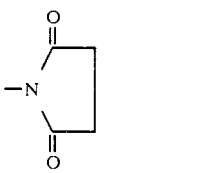 | 5-[2 chloro-4-(trifluoromethyl)phenoxy]-2-nitrobenzoyl 2,5-dioxopyrolidine |

-continued

| | | |
|---|---|---|
| 5 | 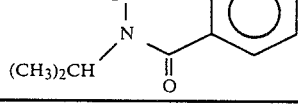 | N—[2-(4,6,6-trimethyl-1,3-thiazinyl)]5-[2-chloro-4-(trifluoromethyl)phenoxy]-2-nitro benzamide |
| 10 | −NHCH₂COH (O) | N—(carboxymethyl)5-[2-chloro-4-(trifluoromethyl)phenoxy]-2-nitro benzamide |
| 15 | −N(CH₃)−CH₂COOH | N—carboxymethyl-N—methyl 5-[2-chloro-4-(trifluoromethyl)phenoxy]-2-nitrobenzamide |
| 20 | (2,5-dichloro-3-methoxycarbonyl)phenyl structure | N—(2,5-dichloro-3-methoxycarbonyl)phenyl 5-[2-chloro-4-(trifluoromethyl)phenoxy]-2-nitrobenzamide |
| 25 | triazinone hydrazide structure | N—[4-[6-(1,1-dimethylethyl)-3-methylthio-1,2,4-triazin-5(4H)—onyl]]5-[2-chloro-4-(trifluoromethyl)phenoxy]-2-nitrobenzamide |
| 30 | dinitrophenyl isopropyl structure | N—(3,4-dimethyl-2,6-dinitrophenyl)-N—(1-methylethyl) 5-[2-chloro-4-(trifluoromethyl)phenoxy]-2-nitrobenzamide |
| 40 | dinitro-CF₃-phenyl ethyl structure | N—[2,6-dinitro-4-(trifluoromethyl)phenyl]-N—ethyl 5-[2-chloro-4-(trifluoromethyl)phenoxy]-2-nitrobenzamide |

H. Other Benzoyl Compounds

The following 5-[2-chloro-4-(trifluoromethyl)-phenoxy]-2-nitro-benzoyl compounds do not readily fall within the defined classes A–G above and are therefore listed below:

Compund 78

2-chloro-cyclohexyl 5-[2-chloro-4-(trifluoromethyl)-phenoxy]-2-nitrobenzoate (oil).

Compound 79

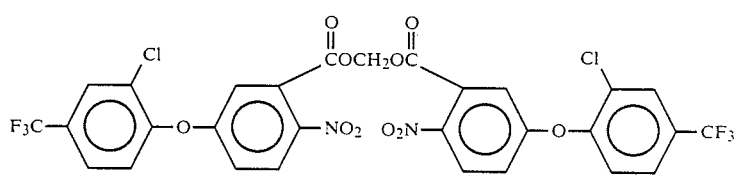

[m.p. 134°-6° C.]

Compound 80

S-(4-chloro-benzyl) 5-[(2-chloro-4-trifluoromethyl)-phenoxy]-2-nitro-benzene carbothioate. [oil]

Compound 81

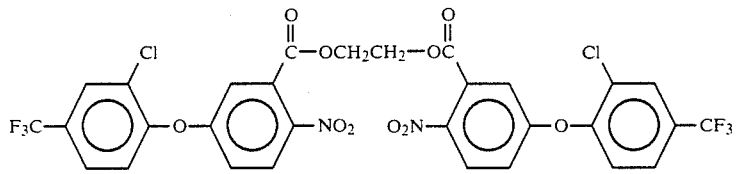

[oil]

Additional illustrative compounds are listed below according to the structural formula:

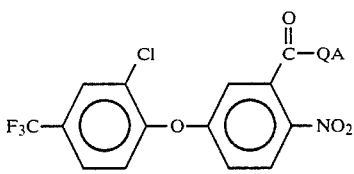

| QA | Compound Name |
|---|---|
| ![COOCH3, F, F biphenyl]-O- | 4-(2,4-difluorophenyl)-2-(methoxycarbonyl)phenyl 5-[2-chloro-4-(trifluoromethyl) phenoxy]-2-nitrobenzoate |
| ![OH, CH2CH2COOC2H5 phenyl]-O- | 4-(ethoxycarbonylethyl)-2-hydroxyphenyl 5-[2 chloro-4(trifluoromethyl)phenoxy]-2-nitrobenzoate |
| ![NO2, N(C3H7)2, NO2 phenyl]-O- | 3,5-dinitro-4-dipropylaminophenyl 5-[2-chloro-4-(trifluoromethyl) phenoxy]-2-nitrobenzoate |
| ![CH2OH, CH3, CH2OH phenyl]-O- | 2,6-bis(hydroxymethyl)-4-methylphenyl 5-[2-chloro-4-(trifluoromethyl)phenoxy]-2-nitrobenzoate |
| ![diisopropylidene-D-glucosyl]-O- | 3-(1,2,5,6-diisopropylidene-D-glucosyl)5-[2-chloro-4-(trifluoromethyl)phenoxy]-2-nitrobenzoate |

-continued

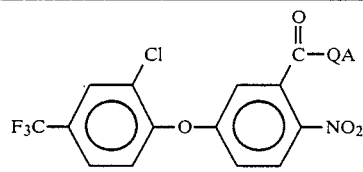

| QA | Compound Name |
|---|---|
| (2-chloro-9-(methoxycarbonyl)-9H-fluoren-9-yl structure with CH₃OOC and Cl substituents, −O− linkage) | 2-chloro-9-(methoxycarbonyl) 9H—fluoran-9-yl 5-[2-chloro-4-(trifluoromethyl)phenyl]-2-nitrobenzoate |
| −OCH(C₆H₅)−C(=O)−C₆H₅ | α-benzoyl (phenylmethyl)5-[2-chloro-4-(trifluoromethyl)phenoxy]-2-nitrobenzoate |
| −OCH₂CH₂NHC(=O)CH₃ | 2-(acetylamino)ethyl 5-[2-chloro-4-(trifluoromethyl)phenoxy]-2-nitrobenzoate |
| −OCH₂CH₂NHC(=O)−C(CH₃)=CH₂ | 2-(2-methylpropanoyl-amino)ethyl 5-[2-chloro-4-(trifluoromethyl)phenoxy]-2-nitrobenzoate |
| −OCH₂CH₂OC(=O)−CH(CH₃)−CH₂N(CH₃)₂ | [3-(dimethylamino)-2-methyl propionyloxy]ethyl 5-[2-chloro-4-(trifluoromethyl) phenoxy]-2-nitrobenzoate |
| −OCH₂CH(CH₃)−OC(=O)−C(CH₃)=CH₂ | 2-(2-methylpropenoyloxy)-2-methylethyl 5-[2-chloro-4-(trifluoromethyl)phenoxy]-2-nitrobenzoate |
| −OCH₂OC(CH₃)₂−C≡N | (1-cyano-1 methyl)ethoxymethyl 5-[2-chloro-4-(trifluoromethyl) phenoxy]-2-nitrobenzoate |
| −OCH(C(=O)CH₃)−C(=O)OC₂H₅ | (ethoxycarbonyl)(acetyl)methyl 5-[2-chloro-4-(trifluoromethyl) phenoxy]-2-nitrobenzoate |
| −OCH₂P(=O)(OCH₂H₅)₂ | diethoxyphosphonylmethyl 5-[2-chloro-4-(trifluoromethyl)phenoxy]-2-nitrobenzoate |
| −OCH₂CH₂P(=O)−(OCH₃)₂ | dimethoxyphosphonylethyl 5-[2-chloro-4-(trifluoromethyl)phenoxy]-nitrobenzoate |
| −OCH₂CH₂OCH₂CH₂P(=O)(OCH₃)₂ | dimethoxyphosphonylethoxy ethyl 5-[2-chloro-4-(trifluoromethyl) phenoxy]-2-nitrobenzoate |

-continued

| QA | Compound Name |
|---|---|
| —OCH$_2$CH$_2$COCH$_2$Cl | 2-(chloroacetyl)ethyl 5-[2-chloro-4-(trifluoromethyl)phenoxy]-2-nitrobenzoate |
| —OCHF$_2$ | difluoromethyl 5-[2-chloro-4-(trifluoromethyl)phenoxy]-2-nitrobenzoate |
| —OCH$_2$NH—CO—CH=CH$_2$ | propenoylaminomethyl 5-[2-chloro-4-(trifluoromethyl)phenoxy]-2-nitrobenzoate |
| —O—CH(CN)—COOC$_2$H$_5$ | cyano(ethoxycarbonyl)methyl 5-[2-chloro-4-(trifluoromethyl)phenoxy]-nitrobenzoate |
| —OCH$_2$C≡CCH$_2$OCNH—(3-Cl-C$_6$H$_4$) | 4-(3-chlorophenylcarbamoyloxy)butyn-2-yl 5-[2-chloro-4-(trifluoromethyl)phenoxy]-2-nitrobenzoate |
| —OCH$_2$—N(2,6-diethylphenyl)(COCH$_2$Cl) | N—(Chloroacetyl)-N—(2,6-diethylphenylamino)methyl 5-[2-chloro-4-(trifluoromethyl)phenoxy]-2-nitrobenzoate |
| —OCH$_2$CH=CHCN | 3-cyanopropen-2-yl 5-[2-chloro-4-(trifluoromethyl)phenoxy]-2-nitrobenzoate |
| —SCN | 5-[2-chloro-4-(trifluoromethyl)phenoxy]-2-nitrobenzoic acid anhydride with thiocyanic acid |
| —SCH$_2$CH$_2$NHSO$_2$—C$_6$H$_5$ | S—(phenylsulfonylaminoethyl)5-[2-chloro-4-(trifluoromethyl)phenoxy]2-nitrobenzenecarbothioate |
| —S—CH$_2$CH(OH)—CH$_2$OH | S(2,3-Dihydroxypropyl)5-[2-chloro-4-(trifluoromethyl)phenoxy]-2-nitrobenzenecarbothioate |
| —SCH$_2$COOC$_2$H$_5$ | S—(ethoxycarbonylmethyl)5-[2-chloro-4-(trifluoromethyl)phenoxy]-2-nitrobenzenecarbothioate |
| —SCH$_2$COOH | S—(carboxymethyl)5-[2-chloro-4-(trifluoromethyl)phenoxy]-2-nitrobenzenecarbothioate |
| —S—CH$_2$—(3-F-C$_6$H$_4$) | S—[(3-fluorophenyl)methyl]5-[2-chloro-4-(trifluoromethyl)phenoxy]-2-nitrobenzenecarbothioate |
| —SCH$_2$CO—SC$_2$H$_5$ | S—[(ethylthiocarbonyl)methyl] 5-[2-chloro-4-(trifluoromethyl)phenoxy]-2-nitrobenzenecarbothioate |

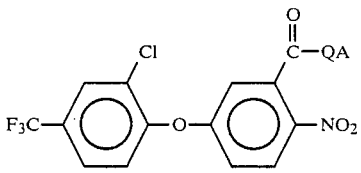

| QA | Compound Name |
|---|---|
| —SCH$_2$C(=O)—OCH$_2$CHCH$_2$OH with OH | S—[2,3-dihydroxypropoxycarbonyl)methyl]5-[2-chloro-4-(trifluoromethyl)phenoxy]-2-nitrobenzenecarbothioate |
| —S—CH$_2$CH=CHCOOC$_2$H$_5$ | S—[(3-ethoxycarbonyl)propen-2-yl] 5-[2-chloro-4-(trifluoromethyl)phenoxy]-2-nitrobenzenecarbothioate |
| —OC(=O)—O—C(CH$_3$)$_2$—CCl$_3$ | 1,1 dimethyl-2,2,2-trichloroethoxycarbonyl 5-[2-chloro-4-(trifluoromethyl)phenoxy]-2-nitrobenzoate |
| —P(=O)(OC$_2$H$_5$)(ONH$_4$) | 5-[2-chloro-4-(trifluoromethyl)phenoxy]-2-nitrobenzoyl O—ethylphosphonic acid ammonium salt |
| —CCl$_3$ | 1-{5-[2-chloro-4-(trifluoromethyl)phenoxy]-2-nitrophenyl}2,2,2,-trichloroethanone |
| —CF$_3$ | 1-{5-[2-chloro-4-(trifluoromethyl)phenoxy]-2-nitrophenyl}2,2,2,-trifluoroethanone |
| —CH$_2$P(=O)(OCH$_3$)$_2$ | dimethyl 5-[2-chloro-4-trifluoromethyl)phenoxy]-2-nitrobenzoyl-methylphosphonate |
| 3-methyl-4-methoxyphenyl | {5-[2-chloro-4-(trifluoromethyl)phenoxy]2-nitrophenyl}4-methoxy-3-methylphenyl methanone |
| —CH$_2$NHCH$_2$P(=O)(OCH$_3$)$_2$ | 1-{5-[2-chloro-4-(trifluoromethyl)phenoxy]-2-nitrophenyl}2-(dimethoxyphosphonylmethylamino)ethanone |
| —CN | 5-[2-chloro-4-(trifluoromethyl)phenoxy]-2-nitrobenzoyl cyanide |

| Miscellaneous - Amide | |
|---|---|
| QA | Compound Name |
| —NHCH$_2$CH(OCH$_3$)$_2$ | N—(2,2-dimethoxyethyl)5-[2-chloro-4-trifluoromethyl)phenoxy]-2-nitrobenzamide |
| —N(CH$_2$COOH)(CH$_2$P(=O)(OH)$_2$) | N—(carboxymethyl)-N—(phosphonomethyl)5-[2-chloro-4-(trifluoromethyl)phenoxy]-2-nitrobenzamide |
| —N(H)—OCH$_2$COOH | N—(carboxymethoxy)5-[2-chloro-4-(trifluoromethyl)phenoxy]-2-nitrobenzamide |
| —N(CH$_2$-phenyl)—CH(CH$_3$)$_2$ | N—(1-methylethyl)-N—phenylmethyl)5-[2-chloro-4-(trifluoromethyl)phenoxy]-2-nitrobenzamide |
| 4-chloro-2-oxobenzothiazoline group | 3{5-[2-chloro-4-(trifluoromethyl)phenoxy]-2-nitrobenzoyl}4-chloro-2-oxobenzothiazoline |

-continued

| Miscellaneous - Amide | |
|---|---|
| QA | Compound Name |
| —NH—C(CH₂OH)₂CH₃ | N—[1,3-dihydroxy-2-methylpropyl] 5-[2-chloro-4-(trifluoromethyl)phenoxy]-2-nitrobenzamide |
| —NH—P(=O)(OC₂H₅)₂ | N—(diethoxyphosphonyl)5-[2-chloro-4-(trifluoromethyl)phenoxy]-2-nitrobenzamide |
| —NHCH₂CH₂SO₃Na | N—(2-sulfoethyl)5-[2-chloro-4-(trifluoromethyl)phenoxy]-2-nitrobenzamide sodium salt |
| —NHCH₂SO₃C₆H₁₃ | N—(2-hexyloxysulfonyl)ethyl 5-[2-chloro-4-(trifluoromethyl)phenoxy]-2-nitrobenzamide |
| —NHCCF₃ (C=O) | N—(trifluoroacetyl)5-[2-chloro-4-(trifluoromethyl)phenoxy]-2-nitrobenzamide |
| —NH—C₆H₄—SO₃H | N—(4-sulfophenyl)5-[2-chloro-4-(trifluoromethyl)phenoxy]-2-nitrobenzamide |
| —NH—C(CH₃)₂CN | N—[(1-cyano-1-methyl)-2-ethyl] 4-[2-chloro-4-(trifluoromethyl)phenoxy]-2-nitrobenzamide |
| —NHC(=O)—OC₂H₅ | N—(ethoxycarbonyl)5-[2-chloro-4-(trifluoromethyl)phenoxy]-2-nitrobenzamide |
| —NH—C₆H₃(CH₃)—SO₂—C₆H₅ | N—[2-methyl-4-(phenylsulfonyl)phenyl]5-[2-chloro-4-(trifluoromethyl)phenoxy]-2-nitrobenzamide |
| —N(COOCH₃)—SO₂—C₆H₄—NH₂ | N—(4-aminophenylsulfonyl)-N—(methoxycarbonyl) 5-[2-chloro-4-(trifluoromethyl)phenoxy]-2-nitrobenzamide |
| NHCH=NOH | N—[(hydroxyimino)methyl] 5-[2-chloro-4-(trifluoromethyl)phenoxy]-2-nitrobenzamide |
| —NHNH₂ | 5-[2-chloro-4-(trifluoromethyl)phenoxy]-2-nitrobenzoic acid hydrazide |
| —N(CH₃)—NH₂ | 5-[2-chloro-4-(trifluoromethyl)phenoxy]-2-nitrobenzoic acid methyl hydrazide |
| —NHNH—CCH₂Cl (C=O) | 5-[2-chloro-4-(trifluoromethyl)phenoxy]-2-nitrobenzoyl(2-chloroacetyl)hydrazide |
| —NHNHCNH₂ (C=O) | 5-[2-chloro-4-(trifluoromethyl)phenoxy]-2-nitrobenzoyl 2-(carboxamido)hydrazide |
| —NHCN | 5-[2-chloro-4-(trifluoromethyl)phenoxy]-2-nitrobenzoylcyanamide |
| —N(Na)—CN | 5-[2-chloro-4-(trifluoromethyl)phenoxy]-2-nitrobenzoylcyanamide sodium salt |
| —N₃ | 5-[2-chloro-4-(trifluoromethyl)phenoxy]-2-nitrobenzoyl amide |
| —O—N=CHNH₂ | aminomethyleneamino 5-[2-chloro-4-(trifluoromethyl)phenoxy]-2 nitrobenzoate |
| —ON=C(CH₃)₂ | 1-methylethylideneimino 5-[2-chloro-4-(trifluoromethyl)phenoxy]-2-nitrobenzoate |
| —ON=C(SCH₃)(CH₃) | 1-(methylthio)ethylideneamino 5[2-chloro-4-(trifluoromethyl)phenoxy]-2-nitrobenzoate |

Primary Herbicide Screening

The compounds of this invention can be applied in various ways to achieve herbicidal action. They can be applied per se, as solids or in vaporized form, but are preferably applied as the toxic components in pesticidal compositions of the compound and a carrier. These compositions are preferably applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil.

In practice, herbicidal application is measured in terms of pounds of herbicide applied per acre. The compounds of this invention are effective herbicides when applied in herbicidal amounts, i.e., at rates between about 0.03 pounds and about 10 pounds per acre.

HERBICIDAL EFFECTIVENESS

Method of Propagating Test Species

Crop and weed species are planted in 8"×10" disposable fiber flats containing potting soil to provide each flat with a 4" row of all test species. Crop species consist of field corn (CN), crabgrass (CG), cotton (CT), and soybeans (SB). The weed species consist of foxtail millet (FM), green foxtail (CF), velvetleaf (VL), cocklebur (CB), wild mustard (WM) and pigweed (FW).

Cotton, corn, soybean, and cocklebur plantings consist of 4 to 5 seeds per row depending upon species. The smaller seeded species (velvetleaf, wild mustard, pigweed, foxtail millet and green foxtail) are planted in an uncounted but sufficient number to provide a solid row of seedlings.

Plantings for the pre- and post-emergence portions of the test are identical as to seeding. The initial watering until emergence is done from the top. The post-emergence phase is propagated in advance so as to provide plants of the proper stage of development at the time of treatment. Plantings for the pre-emergence phase are made not more than one day in advance of treatment.

The desired stage of development for treatment of the post-emergence broadleaf species (CT, SB, CB, VL, WM, PW) is the one true leaf or first trifoliate leaf stage. The desired stage for corn would be a height of 3-4", while a 2" height would be adequate for the grasses.

Method of Treatment

Spray applications are made with a handgun sprayer (aspirator type) simultaneously to one flat of established plants for the post-emergence phase and one newly seeded flat for the pre-emergence phase. The 10 lb./acre treatment rate consists of the uniform application of 116 milligrams of test compound to the combined area of the two flats (160 sq. inches). Application is made in a solvent mixture consisting of 40 ml acetone and 40 ml water and a surfactant concentration of 0.1%.

Following spray application, flats are returned to the greenhouse where watering of the post-emergence phase is done only by subirrigation. The pre-emergence phase is top watered by sprinkling until after test species have emerged. Subsequent watering is by-subirrigation.

Two weeks after treatment, the pre- and post-emergence injury and control is rated on a 0–100% injury and control scale. Special physiological effects are rated as to intensity also at this time.

The herbicidal test data reported for compounds 1–81 was obtained at application rates of 10 lbs. down to ¼ lb./acre. The following lists the metric equivalents for each rate.

| Application Rate | |
|---|---|
| US - lb./acre | Metric - kg/ha |
| 10.0 | 11.2 |
| 4.0 | 4.48 |
| 2.0 | 2.24 |
| 1.0 | 1.12 |
| 0.5 | 0.56 |
| 0.25 | 0.28 |

Test results are set forth in Table I (pre-emergence) and Table II (post-emergence).

TABLE I

| Cpd. No. | Dosage Lbs./Acre | CG | FM | GF | VL | CB | WM | PW | CT | CN | SB |
|---|---|---|---|---|---|---|---|---|---|---|---|
| 1 | 10 | — | 100 | 90 | 90 | 0 | 100 | 100 | 10 | 0 | 0 |
|   | 4 | — | 100 | 90 | 20 | — | 100 | — | 0 | 0 | 0 |
|   | 2 | — | 100 | 60 | 10 | — | 100 | 70 | 0 | 10 | 10 |
|   | 1 | — | 90 | 90 | 30 | 0 | 100 | 100 | 20 | 0 | 10 |
|   | ½ | — | 90 | 80 | 0 | 0 | 90 | 100 | 20 | 0 | 10 |
|   | ¼ | — | 90 | 70 | 30 | 0 | 90 | 80 | 0 | 10 | 0 |
| 2 | 10 | — | 20 | 20 | 10 | 0 | 70 | 90 | 0 | 0 | 0 |
|   | 4 | — | — | — | — | — | — | — | — | — | — |
|   | 2 | — | — | — | — | — | — | — | — | — | — |
|   | 1 | — | — | — | — | — | — | — | — | — | — |
|   | ½ | — | — | — | — | — | — | — | — | — | — |
|   | ¼ | — | — | — | — | — | — | — | — | — | — |
| 3 | 10 | — | 90 | 90 | 0 | 0 | 90 | 100 | 0 | 0 | 0 |
|   | 4 | — | 100 | 90 | 30 | 20 | 90 | 100 | 10 | 0 | 0 |
|   | 2 | — | 60 | 10 | 0 | 10 | 30 | 80 | — | 0 | 0 |
|   | 1 | — | — | — | — | — | — | — | — | — | — |
|   | ½ | — | — | — | — | — | — | — | — | — | — |
|   | ¼ | — | — | — | — | — | — | — | — | — | — |
| 4 | 10 | — | 100 | 90 | 90 | 20 | 100 | 100 | 10 | 0 | 10 |
|   | 4 | — | 100 | 90 | 0 | — | 100 | — | 0 | 0 | 10 |
|   | 2 | — | 90 | 40 | 0 | — | 70 | 60 | 0 | 0 | 0 |
|   | 1 | — | — | — | — | — | — | — | — | — | — |
|   | ½ | — | — | — | — | — | — | — | — | — | — |
|   | ¼ | — | — | — | — | — | — | — | — | — | — |
| 5 | 4 | — | 90 | 90 | 70 | 30 | 100 | 100 | 60 | 0 | 0 |
|   | 2 | — | 90 | 90 | 10 | 40 | 100 | 100 | 20 | 0 | 10 |
|   | 1 | — | 70 | 10 | 0 | 0 | 70 | 100 | 0 | 0 | 10 |
|   | ½ | — | — | — | — | — | — | — | — | — | — |
|   | ¼ | — | — | — | — | — | — | — | — | — | — |
| 6 | 4 | — | 100 | 90 | 70 | 20 | 100 | 100 | 0 | 40 | 0 |
|   | 2 | — | 100 | 90 | 10 | 0 | 100 | 100 | 40 | 0 | 0 |
|   | 1 | — | 90 | 60 | 0 | 40 | 90 | 90 | 30 | 0 | 0 |
|   | ½ | — | 70 | 80 | 10 | 0 | 50 | 90 | 10 | 0 | 10 |
|   | ¼ | — | 20 | 0 | 10 | 10 | 30 | 0 | 0 | 20 | 10 |
| 7 | 4 | — | 0 | 0 | 0 | 0 | 100 | 100 | 40 | 0 | 0 |
|   | 2 | — | 70 | 20 | 0 | 0 | 0 | 70 | 0 | 0 | 0 |
|   | 1 | — | — | — | — | — | — | — | — | — | — |
|   | ½ | — | — | — | — | — | — | — | — | — | — |
|   | ¼ | — | — | — | — | — | — | — | — | — | — |
| 8 | 10 | — | 0 | 0 | 0 | 0 | 0 | 0 | 0 | 30 | 0 |
|   | 4 | — | — | — | — | — | — | — | — | — | — |
|   | 2 | — | — | — | — | — | — | — | — | — | — |
| 9 | 4 | — | 0 | 0 | 0 | — | 10 | 60 | 10 | 0 | 0 |
|   | 2 | — | — | — | — | — | — | — | — | — | — |
|   | 1 | — | — | — | — | — | — | — | — | — | — |
|   | ½ | — | 10 | 0 | 0 | 0 | 50 | 60 | 0 | 0 | 0 |
|   | ¼ | — | — | — | — | — | — | — | — | — | — |
| 10 | 4 | — | 10 | 10 | 10 | 0 | 0 | 0 | 10 | 10 | 10 |
|    | 2 | — | — | — | — | — | — | — | — | — | — |
| 11 | 10 | — | 0 | 0 | 0 | 0 | 0 | 0 | 0 | 0 | 0 |
|    | 4 | — | — | — | — | — | — | — | — | — | — |
| 12 | 4 | — | 100 | 90 | 90 | 60 | 100 | 100 | 40 | 10 | 0 |
|    | 2 | — | 100 | 90 | 40 | 10 | 100 | 100 | 10 | 30 | 0 |
|    | 1 | — | 100 | 90 | 0 | 0 | 100 | 100 | 0 | 0 | 0 |
|    | ½ | — | 70 | 30 | 10 | 0 | 90 | 90 | 30 | 0 | 0 |
|    | ¼ | — | 20 | 20 | 0 | 0 | 20 | 60 | 60 | 60 | 30 |

TABLE I-continued

| Cpd. No. | Dosage Lbs./ Acre | Pre-Emergence | | | | | | | | |
|---|---|---|---|---|---|---|---|---|---|---|
| | | CG | FM | GF | VL | CB | WM | PW | CT | CN | SB |
| 13 | 10 | — | 90 | 90 | 100 | 80 | 100 | 100 | 90 | 10 | 10 |
| | 4 | — | 90 | 90 | 70 | 10 | 90 | 90 | 10 | 20 | 0 |
| | 2 | — | 90 | 70 | 30 | 0 | 90 | 90 | 0 | 0 | 0 |
| | 1 | — | — | — | — | — | — | — | — | — | — |
| | ½ | — | — | — | — | — | — | — | — | — | — |
| | ¼ | — | — | — | — | — | — | — | — | — | — |
| 14 | 4 | — | 70 | 50 | 10 | 0 | 70 | 60 | 0 | 20 | 0 |
| | 1 | — | — | — | — | — | — | — | — | — | — |
| | ½ | — | — | — | — | — | — | — | — | — | — |
| | ¼ | — | — | — | — | — | — | — | — | — | — |
| 15 | 4 | — | 100 | 90 | 40 | 20 | 90 | 90 | 10 | 0 | 0 |
| | 2 | — | 90 | 90 | 10 | 0 | 90 | 90 | 0 | 0 | 0 |
| | 1 | — | 70 | 60 | 10 | 0 | 20 | 80 | 20 | 0 | 10 |
| | ½ | — | — | — | — | — | — | — | — | — | — |
| | ¼ | — | — | — | — | — | — | — | — | — | — |
| 16 | 4 | — | 90 | 50 | 10 | 0 | 90 | 70 | 10 | 10 | 0 |
| | 2 | — | 80 | 10 | 10 | 0 | 70 | 0 | 0 | 0 | 10 |
| | 1 | — | — | — | — | — | — | — | — | — | — |
| | ½ | — | — | — | — | — | — | — | — | — | — |
| | ¼ | — | — | — | — | — | — | — | — | — | — |
| 17 | 4 | — | 100 | 90 | 40 | 0 | 100 | 100 | 0 | 10 | 0 |
| | 2 | — | 90 | 90 | 30 | 0 | 90 | 90 | 30 | 0 | 10 |
| | 1 | — | — | — | — | — | — | — | — | — | — |
| | ½ | — | — | — | — | — | — | — | — | — | — |
| | ¼ | — | — | — | — | — | — | — | — | — | — |
| 18 | 10 | — | 100 | 80 | 70 | 0 | 100 | 100 | 10 | 0 | 0 |
| | 2 | — | 100 | 40 | 20 | 10 | 100 | 100 | 10 | 0 | 10 |
| | ½ | — | 90 | 20 | 0 | 10 | 100 | 90 | 10 | 10 | 30 |
| | ¼ | — | 10 | 10 | 40 | 10 | 80 | 60 | 10 | 0 | 0 |
| 19 | 10 | — | 100 | 100 | 80 | 60 | 100 | 100 | 30 | 60 | 0 |
| | 2 | — | 100 | 70 | 40 | 10 | 100 | 100 | 20 | 10 | 10 |
| | ½ | — | 100 | 60 | 0 | 0 | 100 | 60 | 10 | 0 | 0 |
| | ¼ | — | 10 | 10 | 60 | 20 | 70 | 50 | 20 | 0 | 20 |
| 20 | 4 | — | 90 | 80 | 50 | 0 | 100 | 90 | 0 | 0 | 0 |
| | 2 | — | 80 | 20 | 10 | 20 | 90 | 20 | 0 | 0 | 10 |
| | 1 | — | 0 | 0 | 0 | 0 | 0 | 20 | 30 | 10 | 10 |
| | ½ | — | — | — | — | — | — | — | — | — | — |
| | ¼ | — | — | — | — | — | — | — | — | — | — |
| 21 | 4 | — | 80 | 60 | 20 | 0 | 30 | 20 | 10 | 20 | 20 |
| | 2 | — | — | — | — | — | — | — | — | — | — |
| 22 | 4 | — | 90 | 80 | 20 | 0 | 90 | 90 | 0 | 10 | 0 |
| | 2 | — | 80 | 70 | 20 | 0 | 80 | 60 | 0 | 20 | 0 |
| | 1 | — | 90 | 20 | 10 | 20 | 30 | 10 | 40 | 10 | 50 |
| | ¼ | — | — | — | — | — | — | — | — | — | — |
| 23 | 4 | — | 80 | 0 | 10 | 0 | 90 | 30 | 10 | 0 | 0 |
| | 2 | — | 70 | 10 | 30 | 0 | 70 | 10 | 0 | 0 | 0 |
| | ½ | — | — | — | — | — | — | — | — | — | — |
| | ¼ | — | — | — | — | — | — | — | — | — | — |
| 24 | 4 | — | 90 | 70 | 60 | 10 | 90 | 90 | 0 | 0 | 10 |
| | 2 | — | 80 | 70 | 40 | 0 | 70 | 80 | 0 | 0 | 0 |
| | ½ | — | 0 | 10 | 0 | 0 | 0 | 10 | 0 | 0 | 0 |
| | ¼ | — | — | — | — | — | — | — | — | — | — |
| 25 | 4 | — | 100 | 90 | 90 | 20 | 100 | 100 | 10 | 40 | 10 |
| | 2 | — | 90 | 90 | 80 | 40 | 100 | 100 | 40 | 10 | 20 |
| | 1 | — | 100 | 90 | 10 | 0 | 90 | 90 | 0 | 0 | 0 |
| | ½ | — | 90 | 70 | 0 | 0 | 90 | 70 | 10 | 0 | 10 |
| | ¼ | — | 10 | 20 | 10 | 0 | 20 | 20 | 0 | 0 | 0 |
| 26 | 2 | — | 40 | 40 | 20 | 70 | 90 | 70 | 0 | 0 | 10 |
| | ½ | — | 10 | 0 | 10 | 0 | 90 | 40 | 0 | 0 | 0 |
| | ¼ | — | — | — | — | — | — | — | — | — | — |
| 27 | 2 | — | 90 | 90 | 80 | 0 | 100 | 100 | 10 | 0 | 0 |
| | ½ | — | 70 | 50 | 40 | 0 | 90 | 100 | 0 | 0 | 0 |
| | ¼ | — | 50 | 10 | 0 | 0 | 70 | 10 | 0 | 0 | 0 |
| 28 | 2 | — | 90 | 90 | 90 | 20 | 100 | 100 | 50 | 10 | 20 |
| | ½ | — | 90 | 90 | 20 | 0 | 100 | 100 | 10 | 0 | 0 |
| | ¼ | — | 60 | 20 | 0 | — | 50 | 80 | 10 | 0 | 0 |
| 29 | 2 | — | 100 | 100 | 40 | 10 | 100 | 100 | 0 | 0 | 20 |
| | ½ | — | 100 | 90 | 0 | 0 | 100 | 90 | 10 | 0 | 0 |
| | ¼ | — | 10 | 40 | 60 | 0 | 90 | 90 | 0 | 0 | 0 |
| 30 | ½ | 10 | 60 | — | 30 | — | 90 | 90 | — | — | — |
| | ¼ | 10 | 40 | — | 10 | — | 10 | — | — | — | — |
| 31 | 2 | — | 60 | 50 | 10 | 0 | 80 | 90 | 30 | 20 | 0 |
| | ½ | — | 10 | 0 | 10 | 0 | 10 | 50 | 0 | 0 | 0 |
| | ¼ | — | — | — | — | — | — | — | — | — | — |
| 32 | 2 | — | 90 | 70 | 0 | 0 | 100 | 100 | 10 | 0 | 10 |
| | ½ | — | 90 | 90 | 0 | 0 | 90 | 80 | 0 | 0 | 10 |
| | ¼ | — | 30 | 10 | 0 | 0 | 10 | 0 | 0 | 0 | 0 |
| 33 | 2 | — | 100 | 90 | 50 | 0 | 90 | 90 | 10 | 10 | 40 |
| | ½ | — | 80 | 10 | 0 | 0 | 20 | 10 | 0 | 0 | 0 |

TABLE I-continued

| Cpd. No. | Dosage Lbs./ Acre | Pre-Emergence | | | | | | | | | |
|---|---|---|---|---|---|---|---|---|---|---|---|
| | | CG | FM | GF | VL | CB | WM | PW | CT | CN | SB |
| 34 | 1/4 | — | — | — | — | — | — | — | — | — | — |
| | 2 | — | 100 | 100 | 10 | 30 | 90 | 90 | 30 | 10 | 0 |
| | 1/2 | — | 20 | 20 | 20 | 10 | 80 | 20 | 0 | 0 | 0 |
| 36 | 1/4 | — | — | — | — | — | — | — | — | — | — |
| | 2 | — | 50 | 20 | 40 | — | 20 | 90 | 10 | 20 | 30 |
| | 1/2 | — | 0 | 0 | 0 | — | 20 | 50 | 10 | 10 | 10 |
| 37 | 1/4 | — | — | — | — | — | — | — | — | — | — |
| | 2 | — | 60 | 60 | 0 | — | 80 | 20 | 0 | 0 | 0 |
| | 1/2 | — | 0 | 0 | 0 | — | 0 | 0 | 0 | 0 | 0 |
| 38 | 1/4 | — | — | — | — | — | — | — | — | — | — |
| | 2 | — | 100 | 90 | 50 | 10 | 100 | 100 | 60 | 0 | 0 |
| | 1/2 | — | 90 | 50 | 0 | 0 | 50 | 40 | 0 | 0 | 0 |
| 39 | 1/4 | — | — | — | — | — | — | — | — | — | — |
| | 2 | — | 90 | 90 | 70 | 20 | 100 | 100 | 10 | 20 | 0 |
| | 1/2 | — | 90 | 70 | 10 | 10 | 100 | 100 | 0 | 0 | 0 |
| 40 | 2 | — | 100 | 90 | 90 | 0 | 100 | 100 | 10 | 10 | 0 |
| | 1/2 | — | 90 | 70 | 20 | 0 | 100 | 90 | 10 | 0 | 0 |
| 41 | 2 | — | 100 | 90 | 40 | 0 | 100 | 90 | 10 | 0 | 0 |
| | 1/2 | — | 90 | 30 | 0 | 0 | 90 | 70 | 0 | 0 | 0 |
| | 1/4 | — | 0 | 0 | 0 | 0 | 10 | 10 | 0 | 0 | 0 |
| 42 | 2 | — | 100 | 100 | 90 | 70 | 100 | 100 | 90 | 20 | 30 |
| | 1/2 | — | 100 | 100 | 80 | 60 | 100 | 100 | 90 | 20 | 30 |
| | 1/4 | — | 80 | 90 | 10 | 0 | 60 | 90 | 10 | 0 | 10 |
| 43 | 1/2 | 90 | 90 | — | 50 | 0 | 90 | 100 | — | — | — |
| | 1/4 | 60 | 90 | — | 50 | — | 10 | — | — | — | — |
| 44 | 2 | — | 100 | 100 | 90 | 30 | 100 | 100 | 60 | 20 | 30 |
| | 1/2 | — | 90 | 90 | 80 | 10 | 100 | 100 | 20 | 10 | 20 |
| | 1/4 | — | 20 | 0 | 0 | 0 | 90 | 20 | 0 | 0 | 10 |
| 45 | 2 | — | 100 | 100 | 70 | 10 | 100 | 100 | 10 | 10 | 0 |
| | 1/2 | — | 90 | 80 | 10 | 0 | 100 | 100 | 0 | 0 | 0 |
| | 1/4 | — | 90 | 10 | 0 | 0 | 80 | 90 | 0 | 0 | 0 |
| 46 | 2 | — | 100 | 90 | 20 | 10 | 100 | 90 | 10 | 0 | 0 |
| | 1/2 | — | 90 | 90 | 10 | 30 | 90 | 70 | 10 | 0 | 0 |
| | 1/4 | — | 30 | 20 | 0 | 0 | 0 | 0 | 0 | 0 | 0 |
| 47 | 2 | — | 100 | 90 | 90 | 20 | 100 | 100 | 30 | 10 | 0 |
| | 1/2 | — | 100 | 90 | 20 | 10 | 100 | 100 | 10 | 0 | 0 |
| | 1/4 | — | 20 | 0 | 0 | 0 | 90 | 90 | 20 | 10 | 0 |
| 48 | 2 | — | 100 | 100 | 70 | 100 | 100 | 0 | 0 | 0 | 0 |
| | 1/2 | — | 100 | 90 | 30 | 0 | 90 | 60 | 40 | 0 | 0 |
| 49 | 2 | — | 90 | 90 | 60 | 0 | 90 | 100 | 0 | 0 | 0 |
| | 1/2 | — | 20 | 0 | 10 | 10 | 100 | 90 | 0 | 0 | 10 |
| 50 | 2 | — | 90 | 90 | 90 | 50 | 100 | 100 | 50 | 10 | 30 |
| | 1 | — | 90 | 90 | 20 | 0 | 100 | 90 | 0 | 0 | 0 |
| | 1/2 | — | 80 | 70 | 10 | 0 | 100 | 90 | 10 | 10 | 20 |
| | 1/4 | — | 90 | 70 | 20 | 10 | 90 | 80 | 0 | 0 | 0 |
| 51 | 10 | — | 100 | 100 | 100 | 50 | 100 | 100 | 10 | 30 | 0 |
| | 4 | — | 100 | 100 | 90 | 60 | 100 | 100 | 20 | 10 | 20 |
| | 2 | — | 90 | 90 | 70 | 10 | 100 | 100 | 20 | 0 | 10 |
| | 1 | — | 100 | 100 | 10 | 0 | 100 | 100 | 0 | 0 | 10 |
| | 1/2 | — | 90 | 50 | 0 | 10 | 70 | 40 | 0 | 0 | 0 |
| | 1/4 | — | — | — | — | — | — | — | — | — | — |
| 52 | 10 | 100 | 100 | — | 90 | — | 100 | — | — | — | — |
| | 1 | 60 | 70 | — | 60 | 0 | 90 | — | — | — | — |
| | 1/2 | 40 | 80 | — | 50 | 10 | 80 | — | — | — | — |
| | 1/4 | — | — | — | — | — | — | — | — | — | — |
| 53 | 10 | — | 90 | 90 | 50 | — | 100 | 100 | 50 | 10 | 0 |
| | 4 | — | 90 | 90 | 30 | — | 100 | 100 | 10 | 0 | 0 |
| | 1 | — | 90 | 60 | 0 | — | 90 | 90 | 0 | 0 | 0 |
| | 1/2 | — | 10 | 0 | 10 | — | 20 | 90 | 0 | 0 | 0 |
| | 1/4 | — | — | — | — | — | — | — | — | — | — |
| 54 | 4 | — | 0 | 0 | 0 | 0 | 0 | 0 | 0 | 0 | 0 |
| | 2 | — | — | — | — | — | — | — | — | — | — |
| | 1 | — | — | — | — | — | — | — | — | — | — |
| | 1/2 | — | — | — | — | — | — | — | — | — | — |
| | 1/4 | — | — | — | — | — | — | — | — | — | — |
| 55 | 4 | — | 0 | 20 | 40 | 10 | 90 | 100 | 60 | 0 | 20 |
| | 2 | — | 0 | 0 | 0 | 0 | 0 | 0 | 0 | 0 | 0 |
| | 1 | — | — | — | — | — | — | — | — | — | — |
| | 1/2 | — | — | — | — | — | — | — | — | — | — |
| | 1/4 | — | — | — | — | — | — | — | — | — | — |
| 56 | 4 | — | 0 | 0 | 30 | — | 70 | 100 | 30 | 0 | 0 |
| | 2 | — | — | — | — | — | — | — | — | — | — |
| 57 | 4 | — | 10 | 0 | 0 | — | 70 | 90 | 0 | 0 | 0 |
| | 2 | — | — | — | — | — | — | — | — | — | — |
| | 1 | — | — | — | — | — | — | — | — | — | — |
| | 1/2 | — | — | — | — | — | — | — | — | — | — |
| | 1/4 | — | — | — | — | — | — | — | — | — | — |
| 58 | 4 | — | 30 | 0 | 0 | — | 10 | 100 | 0 | 0 | 0 |
| | 2 | — | — | — | — | — | — | — | — | — | — |

TABLE I-continued

| Cpd. No. | Dosage Lbs./ Acre | Pre-Emergence ||||||||||
| --- | --- | --- | --- | --- | --- | --- | --- | --- | --- | --- | --- |
| | | CG | FM | GF | VL | CB | WM | PW | CT | CN | SB |
| | 1 | — | — | — | — | — | — | — | — | — | — |
| 59 | 10 | — | 0 | 0 | 0 | — | 0 | 100 | 0 | 0 | 0 |
| 60 | 10 | — | 0 | 0 | 10 | 0 | 10 | 70 | 0 | 0 | 0 |
| | 4 | — | — | — | — | — | — | — | — | — | — |
| 61 | 2 | — | 50 | 20 | 60 | 10 | 90 | 80 | 20 | 10 | 20 |
| | ½ | — | 0 | 0 | 0 | 0 | 50 | 0 | 0 | 0 | 0 |
| | ¼ | — | — | — | — | — | — | — | — | — | — |
| 62 | 4 | 90 | 100 | — | 80 | — | 100 | 100 | — | — | — |
| | 1 | 90 | 40 | — | 70 | — | 100 | 100 | — | — | — |
| | ½ | 40 | 0 | — | 10 | 0 | 80 | — | — | — | — |
| 63 | 4 | 90 | 90 | — | 100 | — | 100 | 100 | — | — | — |
| | 1 | 60 | 40 | — | 70 | — | 90 | 0 | — | — | — |
| | ½ | 20 | 0 | — | 20 | 0 | 10 | 0 | — | — | — |
| 64 | 4 | 90 | 90 | — | 90 | — | 100 | 100 | — | — | — |
| | 2 | 90 | 90 | — | 50 | — | 100 | 90 | — | — | — |
| | 1 | 20 | 0 | — | 40 | 0 | 90 | 0 | — | — | — |
| | ½ | 0 | 20 | — | 0 | 0 | 70 | 70 | — | — | — |
| 65 | 4 | 80 | 90 | — | 90 | — | 100 | — | — | — | — |
| | 2 | — | 30 | 70 | 20 | 0 | 80 | 100 | 0 | 0 | 0 |
| | 1 | — | 90 | 70 | 80 | 0 | 90 | 90 | 10 | 10 | 0 |
| | ½ | — | 10 | 10 | 50 | 0 | 100 | 100 | 0 | 0 | 0 |
| | ¼ | — | 30 | 10 | 10 | 0 | 70 | 80 | 0 | 0 | 0 |
| 66 | 4 | 90 | 90 | — | 100 | — | 100 | 100 | — | — | — |
| | 1 | 70 | 40 | — | 70 | — | 100 | 100 | — | — | — |
| | ½ | 0 | 10 | — | 20 | 0 | 60 | 0 | — | — | — |
| 67 | 4 | 90 | 90 | — | 90 | — | 100 | 100 | — | — | — |
| | 2 | 60 | 70 | — | 60 | — | 90 | 90 | — | — | — |
| | 1 | 0 | 0 | — | 10 | 0 | 40 | 0 | — | — | — |
| | ½ | 0 | 0 | — | 40 | 10 | 90 | 20 | — | — | — |
| 68 | 10 | 100 | 90 | — | 100 | — | 100 | 100 | — | — | — |
| | 4 | — | 100 | 90 | 90 | 60 | 100 | 100 | 0 | 10 | 0 |
| | 2 | — | 90 | 90 | 90 | 10 | 100 | 100 | 20 | 20 | 20 |
| | 1 | — | 90 | 30 | 90 | 0 | 100 | 100 | 40 | 0 | 0 |
| | ½ | — | 70 | 80 | 70 | 50 | 100 | 100 | 10 | 0 | 0 |
| | ¼ | — | 80 | 60 | 0 | 0 | 100 | 100 | 20 | 0 | — |
| 69 | 2 | — | 100 | 90 | 60 | 50 | 100 | 100 | 10 | 40 | 20 |
| | ½ | — | 100 | 90 | 10 | 10 | 100 | 100 | 0 | 0 | 10 |
| | ¼ | — | 0 | 60 | 10 | 10 | 80 | 80 | 10 | 50 | 10 |
| 70 | 2 | — | 100 | 90 | 50 | 50 | 100 | 100 | 10 | 10 | 20 |
| | ½ | — | 100 | 90 | 10 | 30 | 100 | 100 | 20 | 0 | 10 |
| | ¼ | — | 0 | 10 | 50 | 0 | 90 | 90 | 0 | 40 | 80 |
| 71 | 2 | — | 90 | 50 | 40 | 0 | 90 | 80 | 10 | 10 | 10 |
| | ½ | — | 10 | 10 | 0 | 0 | 10 | 90 | 10 | 0 | 10 |
| | ¼ | — | — | — | — | — | — | — | — | — | — |
| 72 | 10 | — | 90 | 90 | — | 20 | 90 | 90 | — | 40 | 70 |
| | 2 | — | 90 | 90 | 70 | 0 | 100 | 100 | 10 | 20 | 0 |
| | 1 | — | 90 | 80 | 0 | 0 | 90 | 80 | 10 | 0 | 0 |
| | ½ | — | 20 | 0 | 10 | — | 90 | 90 | 20 | 20 | 10 |
| | ¼ | — | 30 | 0 | 10 | — | 70 | 80 | 0 | 20 | 10 |
| 73 | 10 | — | 100 | 90 | 90 | 30 | 100 | 100 | 20 | 60 | 0 |
| | 4 | — | 100 | 90 | 80 | 60 | 100 | 90 | 50 | 70 | 10 |
| | 2 | — | 80 | 70 | 70 | 10 | 100 | 10 | 10 | 0 | 0 |
| | 1 | — | 90 | 60 | 10 | 0 | 90 | 60 | 20 | 0 | 10 |
| | ½ | — | 90 | 50 | 0 | 0 | 90 | 80 | 0 | 0 | 0 |
| 74 | 2 | — | 90 | 90 | 70 | 0 | 100 | 100 | 10 | 10 | 0 |
| | ½ | — | 90 | 70 | 0 | 0 | 90 | 50 | 10 | 0 | 0 |
| | ¼ | — | 0 | 0 | 10 | 0 | 70 | 70 | 10 | 0 | 10 |
| 75 | 2 | — | 60 | 20 | 0 | 0 | 50 | 80 | 0 | 0 | 0 |
| | 1 | — | — | — | — | — | — | — | — | — | — |
| | ½ | — | — | — | — | — | — | — | — | — | — |
| | ¼ | — | — | — | — | — | — | — | — | — | — |
| 76 | 2 | — | 80 | 40 | 80 | 0 | 70 | 70 | 20 | 60 | 10 |
| | ½ | — | 10 | 10 | 0 | 0 | 70 | 70 | 10 | 0 | 0 |
| | ¼ | — | — | — | — | — | — | — | — | — | — |
| 77 | 2 | — | 100 | 90 | 10 | 0 | 100 | 90 | 0 | 0 | 0 |
| | ½ | — | 90 | 70 | 0 | 10 | 90 | 60 | 10 | 0 | 0 |
| 78 | 10 | 90 | 90 | — | 100 | — | 100 | — | — | — | — |
| | 4 | — | 90 | 90 | 90 | 0 | 100 | 100 | 0 | 0 | 0 |
| | 2 | — | 90 | 90 | 80 | 0 | 90 | 100 | 10 | 0 | 0 |
| | 1 | — | 40 | 60 | 60 | 10 | 100 | 100 | 0 | 0 | 0 |
| | ½ | — | 50 | 70 | 0 | — | 90 | 90 | 0 | 0 | 0 |
| | ¼ | — | 80 | 50 | 20 | 0 | 90 | 60 | 10 | 30 | 0 |
| 79 | 10 | 70 | 90 | — | 50 | — | 90 | — | — | — | — |
| | ¼ | 0 | 0 | —. | 0 | — | 0 | — | — | — | — |
| 80 | 4 | — | 100 | 90 | 40 | 20 | 90 | 90 | 0 | 20 | 10 |
| | 2 | — | 90 | 80 | 10 | 10 | 90 | 10 | 10 | 10 | 10 |
| | 1 | — | 10 | 0 | 0 | 0 | 70 | 20 | 0 | 0 | 0 |
| | ½ | — | — | — | — | — | — | — | — | — | — |
| | ¼ | — | — | — | — | — | — | — | — | — | — |

TABLE I-continued

| Cpd. No. | Dosage Lbs./Acre | Pre-Emergence | | | | | | | | | |
|---|---|---|---|---|---|---|---|---|---|---|---|
| | | CG | FM | GF | VL | CB | WM | PW | CT | CN | SB |
| 81 | 2 | — | 80 | 50 | 0 | 0 | 90 | 80 | 0 | 0 | 0 |
| | ½ | — | 10 | 0 | 0 | 0 | 10 | 60 | 0 | 0 | 0 |
| | ¼ | — | — | — | — | — | — | — | — | — | — |

TABLE II

| Cpd. No. | Dosage Lbs./Acre | Post-Emergence | | | | | | | | | |
|---|---|---|---|---|---|---|---|---|---|---|---|
| | | CG | FM | GF | VL | CB | WM | PW | CT | CN | SB |
| 1 | 10 | — | 100 | 100 | 100 | 100 | 100 | 100 | 100 | 80 | 60 |
| | 4 | — | 90 | 90 | 100 | 100 | 100 | 100 | 90 | 60 | 50 |
| | 2 | — | 100 | 100 | 100 | — | 100 | — | 90 | 50 | 20 |
| | 1 | — | 100 | 90 | 100 | — | 100 | 100 | 90 | 30 | 50 |
| | ½ | — | 100 | 90 | 90 | 90 | 100 | 100 | 80 | 70 | 10 |
| | ¼ | — | 50 | 50 | 40 | 80 | 100 | 100 | 60 | 50 | 40 |
| 2 | 10 | — | 90 | 90 | 90 | 80 | 90 | 100 | 90 | 10 | 10 |
| | 4 | — | 100 | 90 | 90 | 60 | 90 | 90 | 90 | 10 | 10 |
| | 2 | — | 90 | 90 | 90 | 80 | 100 | 100 | 90 | 20 | 20 |
| | 1 | — | 90 | 90 | 80 | 90 | 90 | 100 | 90 | 70 | 70 |
| | ½ | — | 80 | 70 | 60 | 90 | 100 | 100 | 90 | 80 | 30 |
| | ¼ | — | 90 | 70 | 70 | 80 | 100 | 80 | 90 | 50 | 60 |
| 3 | 10 | — | 90 | 90 | 90 | 90 | 100 | 100 | 100 | 30 | 30 |
| | 4 | — | 100 | 100 | 90 | 90 | 100 | 100 | 90 | 30 | 10 |
| | 2 | — | 100 | 90 | 100 | 90 | 100 | 100 | 90 | 90 | 20 |
| | 1 | — | 90 | 90 | 90 | 90 | 100 | 100 | 80 | 70 | 60 |
| | ½ | — | 90 | 90 | 90 | 90 | 100 | 90 | 90 | 90 | 60 |
| | ¼ | — | 90 | 80 | 90 | 80 | 100 | 100 | 90 | 30 | 10 |
| 4 | 10 | — | 100 | 100 | 100 | 100 | 100 | 100 | 100 | 90 | 50 |
| | 4 | — | 100 | 100 | 100 | — | 100 | — | 100 | 90 | 30 |
| | 2 | — | 90 | 90 | 100 | 100 | 100 | 100 | 100 | 20 | 20 |
| | 1 | — | 100 | 100 | 100 | — | 100 | 100 | 100 | 40 | 50 |
| | ½ | — | 100 | 90 | 90 | 90 | 100 | 100 | 100 | 70 | 10 |
| | ¼ | — | 50 | 70 | 30 | 50 | 90 | 100 | 40 | 30 | 50 |
| 5 | 4 | — | 100 | 90 | 100 | 100 | 100 | 100 | 90 | 0 | 40 |
| | 2 | — | 90 | 90 | 100 | — | 100 | — | 90 | 10 | 20 |
| | 1 | — | 90 | 90 | 100 | 0 | 100 | 100 | 90 | 50 | 10 |
| | ½ | — | 80 | 70 | 90 | 80 | 100 | 100 | 90 | 20 | 20 |
| | ¼ | — | 60 | 60 | 50 | 70 | 90 | 100 | 60 | 30 | 60 |
| 6 | 4 | — | 100 | 100 | 100 | 100 | 100 | 100 | 100 | 10 | 60 |
| | 2 | — | 100 | 100 | 100 | 100 | 100 | 100 | 90 | 80 | 40 |
| | 1 | — | 70 | 80 | 70 | 70 | 100 | 100 | 60 | 70 | 60 |
| | ½ | — | 90 | 90 | 90 | 90 | 100 | 90 | 80 | 80 | 20 |
| | ¼ | — | 80 | 60 | 80 | 50 | 90 | 70 | 90 | 10 | 10 |
| 7 | 4 | — | 100 | 80 | 100 | 80 | 100 | 100 | 80 | 0 | 20 |
| | 2 | — | 90 | 30 | 100 | — | 90 | 100 | 90 | 10 | 20 |
| | 1 | — | 90 | 70 | 100 | — | 90 | 100 | 90 | — | 40 |
| | ½ | — | 90 | 90 | 100 | — | 90 | 100 | 90 | 10 | 50 |
| | ¼ | — | 90 | 90 | 90 | 50 | 100 | 100 | 60 | 30 | 40 |
| 8 | 10 | — | 90 | 80 | 100 | 60 | 90 | 100 | 40 | 0 | 20 |
| | 4 | — | 60 | 30 | — | — | 70 | — | 70 | 20 | 0 |
| | 2 | — | 80 | 70 | 50 | — | 70 | 70 | 90 | 0 | 10 |
| 9 | 4 | — | 90 | 90 | 100 | 40 | 90 | 100 | 90 | 10 | 20 |
| | 2 | — | 90 | 90 | 90 | — | 90 | 100 | 90 | 10 | 30 |
| | 1 | — | 90 | 90 | 100 | 80 | 100 | 100 | 90 | 0 | 10 |
| | ½ | — | 100 | 90 | 90 | 70 | 100 | 100 | 80 | 10 | 10 |
| | ¼ | — | 70 | 80 | 30 | 50 | 90 | 100 | 50 | 50 | 40 |
| 10 | 4 | — | 80 | 20 | 70 | 10 | 90 | 50 | 90 | 40 | 10 |
| | 2 | — | 50 | 50 | 70 | 0 | 90 | 70 | 90 | 70 | 30 |
| 11 | 10 | — | 90 | 90 | 70 | 30 | 80 | 100 | 40 | 0 | 10 |
| | 4 | — | 30 | 20 | 30 | 20 | 70 | 90 | 80 | 30 | 10 |
| 12 | 4 | — | 90 | 90 | 100 | 90 | 100 | 100 | 90 | 20 | 10 |
| | 2 | — | 100 | 100 | 90 | 100 | 100 | 100 | 100 | 70 | 40 |
| | 1 | — | 100 | 100 | 100 | 100 | 100 | 100 | 100 | 60 | 10 |
| | ½ | — | 100 | 100 | 90 | 80 | 100 | 100 | 80 | 80 | 60 |
| | ¼ | — | 90 | 90 | 90 | 70 | 100 | 100 | 90 | 60 | 50 |
| 13 | 10 | — | 90 | 90 | 100 | 100 | 100 | 100 | 90 | 80 | 20 |
| | 4 | — | 100 | 100 | 100 | 100 | 100 | 100 | 100 | 90 | 90 |
| | 2 | — | 100 | 100 | 90 | 90 | 100 | 100 | 100 | 90 | 50 |
| | 1 | — | 90 | 90 | 90 | 70 | 100 | 100 | 90 | 70 | 50 |
| | ½ | — | 90 | 90 | 80 | 70 | 100 | 100 | 90 | 70 | 60 |
| | ¼ | — | 90 | 80 | 80 | 80 | 100 | 90 | 90 | 60 | 60 |
| 14 | 4 | — | 90 | 90 | 90 | 80 | 100 | 100 | 90 | 30 | 20 |
| | 1 | — | 90 | 90 | 80 | 10 | 90 | 90 | 90 | 70 | 40 |
| | ½ | — | 90 | 90 | 70 | 70 | 90 | 90 | 80 | 70 | 20 |
| | ¼ | — | 80 | 80 | 70 | 50 | 90 | 100 | 80 | 50 | 70 |
| 15 | 4 | — | 90 | 100 | 100 | 90 | 100 | 100 | 100 | 60 | 10 |
| | 2 | — | 90 | 90 | 90 | 90 | 100 | 90 | 90 | 70 | 30 |

TABLE II-continued

| Cpd. No. | Dosage Lbs./Acre | Post-Emergence | | | | | | | | | |
|---|---|---|---|---|---|---|---|---|---|---|---|
| | | CG | FM | GF | VL | CB | WM | PW | CT | CN | SB |
| | 1 | — | 90 | 90 | 80 | 60 | 90 | 100 | 90 | 50 | 30 |
| | ½ | — | 90 | 90 | 90 | 90 | 100 | 100 | 90 | 50 | 30 |
| | ¼ | — | 90 | 70 | 60 | 50 | 70 | 90 | 70 | 50 | 70 |
| 16 | 4 | — | 90 | 90 | 60 | 50 | 100 | 100 | 90 | 50 | 10 |
| | 2 | — | 30 | 40 | 60 | 30 | 90 | 80 | 70 | 50 | 80 |
| | 1 | — | 70 | 60 | 70 | 70 | 90 | 90 | 90 | 60 | 70 |
| | ½ | — | 90 | 70 | 70 | 80 | 100 | 100 | 90 | 60 | 40 |
| | ¼ | — | 60 | 40 | 60 | 30 | 90 | 100 | 60 | 50 | 50 |
| 17 | 4 | — | 100 | 100 | 100 | 90 | 100 | 100 | 90 | 70 | 30 |
| | 2 | — | 100 | 100 | 100 | 90 | 100 | 100 | 100 | 80 | 40 |
| | 1 | — | 90 | 90 | 80 | 60 | 90 | 100 | 70 | 70 | 40 |
| | ½ | — | 90 | 90 | 90 | 90 | 90 | 90 | 90 | 70 | 10 |
| | ¼ | — | 80 | 80 | 80 | 50 | 90 | 60 | 90 | 40 | 10 |
| 18 | 10 | — | 100 | 100 | 100 | 90 | 100 | 100 | 90 | 90 | 90 |
| | 2 | — | 90 | 90 | 100 | 90 | 100 | 100 | 90 | 90 | 80 |
| | ½ | — | 90 | 90 | 100 | 70 | 100 | 100 | 80 | 70 | 60 |
| | ¼ | — | 90 | 70 | 90 | 50 | 100 | 100 | 70 | 70 | 50 |
| 19 | 10 | — | 100 | 100 | 100 | 90 | 100 | 100 | 90 | 80 | 40 |
| | 2 | — | 90 | 90 | 100 | 100 | 100 | 100 | 90 | 60 | 40 |
| | ½ | — | 90 | 90 | 90 | 90 | 100 | 100 | 90 | 80 | 40 |
| | ¼ | — | 90 | 70 | 70 | 40 | 100 | 100 | 50 | 60 | 20 |
| 20 | 4 | — | 90 | 90 | 90 | 80 | 100 | 100 | 90 | 40 | 20 |
| | 2 | — | 70 | 80 | 90 | 70 | 90 | 90 | 90 | 60 | 40 |
| | 1 | — | 80 | 60 | 70 | 70 | 90 | 80 | 90 | 50 | 20 |
| | ½ | — | 20 | 20 | 60 | 30 | 90 | 90 | 90 | 30 | 30 |
| | ¼ | — | 50 | 40 | 40 | 40 | 100 | 50 | 50 | 40 | 50 |
| 21 | 4 | — | 80 | 70 | 90 | 40 | 90 | 90 | 90 | 50 | 20 |
| | 2 | — | 10 | 20 | 70 | 70 | 80 | 70 | 70 | 30 | 30 |
| 22 | 4 | — | 90 | 90 | 90 | 70 | 90 | 100 | 90 | 80 | 30 |
| | 2 | — | 80 | 80 | 90 | 20 | 90 | 100 | 90 | 80 | 50 |
| | 1 | — | 90 | 90 | 70 | 40 | 90 | — | 60 | 50 | 70 |
| | ¼ | — | 50 | 60 | 10 | 10 | 80 | 80 | 50 | 10 | 10 |
| 23 | 4 | — | 90 | 90 | 80 | 60 | 90 | 100 | 90 | 80 | 80 |
| | 2 | — | 90 | 90 | 90 | 70 | 90 | — | 90 | 40 | 40 |
| | ½ | — | 20 | 20 | 20 | 10 | 90 | 80 | 80 | 10 | 10 |
| | ¼ | — | 70 | 70 | 30 | 20 | 80 | 70 | 80 | 10 | 30 |
| 24 | 4 | — | 100 | 100 | 100 | 90 | 100 | 100 | 90 | 90 | 90 |
| | 2 | — | 100 | 100 | 100 | 80 | 100 | — | 90 | 50 | 70 |
| | ½ | — | 60 | 50 | 70 | 20 | 80 | 100 | 90 | 20 | 30 |
| | ¼ | — | 70 | 80 | 70 | 50 | 90 | 90 | 90 | 10 | 40 |
| 25 | 4 | — | 100 | 100 | 100 | 100 | 100 | 100 | 100 | 90 | 80 |
| | 2 | — | — | — | — | — | — | — | — | — | — |
| | 1 | — | 100 | 100 | 100 | 90 | 100 | 90 | 100 | 90 | 70 |
| | ½ | — | 90 | 90 | 90 | 90 | 100 | 100 | 100 | 90 | 90 |
| | ¼ | — | 80 | 80 | 90 | 80 | 90 | 90 | 90 | 40 | 30 |
| 26 | 2 | — | 50 | 70 | 100 | 90 | 100 | 100 | 90 | 30 | 60 |
| | ½ | — | 10 | 0 | 90 | 50 | 90 | 90 | 50 | 20 | 40 |
| | ¼ | — | 20 | 10 | 60 | 80 | 90 | 100 | 50 | 10 | 50 |
| 27 | 2 | — | 100 | 100 | 100 | 100 | 100 | 100 | 90 | 70 | 90 |
| | ½ | — | 100 | 100 | 100 | 90 | 100 | 100 | 90 | 60 | 60 |
| | ¼ | — | 70 | 60 | 90 | 70 | 100 | 60 | 90 | 50 | 80 |
| 28 | 2 | — | 100 | 90 | 100 | 100 | 100 | 100 | 100 | 90 | 90 |
| | ½ | — | 90 | 90 | 90 | 90 | 100 | 100 | 90 | 90 | 60 |
| | ¼ | — | 90 | 90 | 90 | 80 | 100 | 100 | 70 | 90 | 80 |
| 29 | 2 | — | 100 | 100 | 100 | 90 | 100 | 100 | 100 | 60 | 90 |
| | ½ | — | 90 | 90 | 100 | 80 | 100 | 100 | 90 | 10 | 80 |
| | ¼ | — | 90 | 90 | 100 | 70 | 100 | 100 | 90 | 50 | 80 |
| 30 | ½ | 20 | 100 | — | — | — | 100 | 100 | 90 | 80 | 60 |
| | ¼ | 90 | 90 | — | 70 | 100 | 100 | 100 | 90 | 20 | 40 |
| 31 | 2 | — | 90 | 90 | 100 | 90 | 100 | 100 | 90 | 30 | 60 |
| | ½ | — | 90 | 90 | 100 | 70 | 90 | 100 | 90 | 60 | 30 |
| | ¼ | — | 80 | 80 | 100 | 60 | 80 | 100 | 80 | 30 | 70 |
| 32 | 2 | — | 100 | 100 | 100 | 90 | 100 | 100 | 100 | 40 | 80 |
| | ½ | — | 100 | 100 | 100 | 80 | 100 | 100 | 100 | 20 | 80 |
| | ¼ | — | 30 | 20 | 100 | 90 | 90 | 90 | 70 | 60 | 40 |
| 33 | 2 | — | 100 | 100 | 100 | 90 | 100 | 100 | 100 | 70 | 80 |
| | ½ | — | 90 | 90 | 100 | 70 | 100 | 100 | 100 | 70 | 80 |
| | ¼ | — | 80 | 70 | 90 | 90 | 100 | 100 | 70 | 10 | 40 |
| 34 | 2 | — | 70 | 70 | 100 | 90 | 100 | 100 | 90 | 60 | 60 |
| | ½ | — | 60 | 60 | 100 | 90 | 100 | 100 | 80 | 40 | 40 |
| | ¼ | — | 90 | 70 | 90 | 90 | 100 | 100 | 50 | 20 | 50 |
| 36 | 2 | — | 100 | 90 | 90 | 80 | 100 | 100 | 90 | 90 | 50 |
| | ½ | — | 90 | 90 | 90 | 30 | 90 | 100 | 90 | 70 | 60 |
| | ¼ | — | 20 | 30 | 90 | — | 90 | 100 | 90 | 40 | 10 |
| 37 | 2 | — | 90 | 90 | 80 | 0 | 90 | 90 | 90 | 80 | 70 |
| | ½ | — | 90 | 90 | 90 | — | 90 | 90 | 90 | 40 | 40 |
| | ¼ | — | 10 | 10 | 70 | — | 80 | 70 | 50 | 10 | 30 |
| 38 | 2 | — | 90 | 90 | 100 | 90 | 100 | 100 | 90 | 50 | 60 |
| | ½ | — | 90 | 90 | 100 | 90 | 100 | 100 | 60 | 10 | 50 |

TABLE II-continued

| Cpd. No. | Dosage Lbs./Acre | Post-Emergence | | | | | | | | | |
|---|---|---|---|---|---|---|---|---|---|---|---|
| | | CG | FM | GF | VL | CB | WM | PW | CT | CN | SB |
| | ¼ | — | 30 | 20 | 90 | 80 | 100 | 100 | 70 | 10 | 10 |
| 39 | 2 | — | 90 | 90 | 100 | 100 | 100 | 100 | 100 | 60 | 90 |
| | ½ | — | 90 | 90 | 90 | 90 | 100 | 100 | 100 | 40 | 70 |
| 40 | 2 | — | 100 | 100 | 100 | 100 | 100 | 100 | 100 | 90 | 90 |
| | ½ | — | 90 | 90 | 100 | 90 | 100 | 100 | 100 | 30 | 70 |
| 41 | 2 | — | 100 | 100 | 100 | 100 | 100 | 100 | 100 | 90 | 90 |
| | ½ | — | 90 | 90 | 100 | 90 | 100 | 90 | 90 | 30 | 80 |
| | ¼ | — | 70 | 80 | 90 | 70 | 100 | 90 | 90 | 20 | 60 |
| 42 | 2 | — | 100 | 100 | 100 | 100 | 100 | 100 | 100 | 100 | 90 |
| | ½ | — | 100 | 100 | 90 | 90 | 100 | 100 | 100 | 90 | 90 |
| | ¼ | — | 100 | 100 | 100 | 80 | 100 | 100 | 90 | 50 | 80 |
| 43 | ½ | 70 | 100 | — | 90 | 100 | 100 | 100 | 100 | 40 | 40 |
| | ¼ | 100 | 100 | — | 90 | 100 | 100 | 100 | 70 | 40 | 30 |
| 44 | 2 | — | 100 | 100 | 100 | 100 | 100 | 100 | 100 | 90 | 90 |
| | ½ | — | 100 | 100 | 100 | 90 | 100 | 100 | 90 | 80 | 80 |
| | ¼ | — | 90 | 90 | 90 | 70 | 100 | 100 | 90 | 60 | 60 |
| 45 | 2 | — | 100 | 100 | 100 | 100 | 100 | 100 | 100 | 100 | 90 |
| | ½ | — | 100 | 100 | 90 | 90 | 100 | 100 | 100 | 80 | 60 |
| | ¼ | — | 100 | 100 | 90 | 90 | 100 | 100 | 90 | 50 | 60 |
| 46 | 2 | — | 100 | 100 | 100 | 90 | 100 | 100 | 100 | 90 | 90 |
| | ½ | — | 100 | 100 | 100 | 70 | 90 | 90 | 100 | 70 | 50 |
| | ¼ | — | 90 | 90 | 90 | 30 | 90 | 90 | 90 | 50 | 50 |
| 47 | 2 | — | 100 | 100 | 100 | 100 | 100 | 100 | 100 | 90 | 80 |
| | ½ | — | 90 | 90 | 70 | 90 | 100 | 100 | 90 | 50 | 30 |
| | ¼ | — | 90 | 90 | 60 | 20 | 100 | 100 | 80 | 20 | 60 |
| 48 | 2 | — | 100 | 100 | 100 | 90 | 100 | 100 | 100 | 90 | 80 |
| | ½ | — | 90 | 90 | 90 | 90 | 100 | 100 | 100 | 40 | 90 |
| 49 | 2 | — | 50 | 10 | 90 | 70 | 100 | 100 | 60 | 20 | 30 |
| | ½ | — | 10 | 20 | 70 | 30 | 100 | 100 | 90 | 40 | 30 |
| 50 | 2 | — | 90 | 90 | 60 | 90 | 100 | 100 | 90 | 70 | 40 |
| | 1 | — | 90 | 90 | 100 | 100 | 100 | 100 | 80 | 90 | 60 |
| | ½ | — | 60 | 80 | 90 | 70 | 100 | 100 | 80 | 0 | 10 |
| | ¼ | — | 90 | 80 | 90 | 70 | 100 | 100 | 40 | 0 | 30 |
| 51 | 10 | — | 100 | 100 | 100 | 80 | 100 | 100 | 90 | 70 | 70 |
| | 4 | — | 100 | 100 | 100 | 100 | 100 | 100 | 90 | 90 | 70 |
| | 2 | — | 90 | 90 | 100 | 90 | 100 | 100 | 90 | 70 | 40 |
| | 1 | — | 100 | 100 | 100 | 100 | 100 | 100 | 80 | 90 | 80 |
| | ½ | — | 60 | 80 | 100 | 80 | 100 | 100 | 90 | 10 | 20 |
| | ¼ | — | 100 | 90 | 100 | 70 | 100 | 90 | 50 | 0 | 40 |
| 52 | 10 | 70 | 90 | — | 100 | — | 100 | 100 | 80 | 30 | 30 |
| | 1 | 70 | 40 | — | 100 | 50 | 100 | 100 | 80 | 10 | 40 |
| | ½ | 30 | 20 | — | 70 | 20 | 90 | 100 | 40 | 10 | 10 |
| | ¼ | 20 | 90 | — | 30 | 20 | 100 | 100 | 70 | 30 | 10 |
| 53 | 10 | 100 | 100 | — | 100 | 90 | 100 | 100 | 100 | 90 | 90 |
| | 4 | 100 | 90 | — | 80 | 80 | 100 | 100 | 100 | 70 | 80 |
| | 1 | 90 | 90 | — | 70 | 60 | 100 | 100 | 90 | 60 | 50 |
| | ½ | 40 | 40 | — | 20 | 0 | 100 | 90 | 80 | 20 | 50 |
| | ¼ | 20 | 10 | — | 10 | — | 90 | 50 | 20 | 10 | 30 |
| 54 | 4 | — | 30 | 30 | 80 | 30 | 100 | 100 | 40 | 10 | 10 |
| | 2 | — | 20 | 20 | 10 | — | 90 | 90 | 20 | 10 | 10 |
| | 1 | — | 80 | 80 | 90 | 40 | 90 | 90 | 50 | 10 | 20 |
| | ½ | — | 60 | 50 | 10 | — | 90 | 90 | 30 | 10 | 10 |
| | ¼ | — | 20 | 40 | 30 | 50 | 80 | 60 | 40 | 40 | 10 |
| 55 | 4 | — | 20 | 20 | 10 | 20 | 100 | 100 | — | 0 | 10 |
| | 2 | — | 30 | 30 | 0 | — | 100 | 80 | 20 | 0 | 80 |
| | 1 | — | 80 | 80 | 20 | 30 | 90 | 100 | 30 | 20 | 30 |
| | ½ | — | 80 | 80 | 10 | — | 90 | — | 80 | 0 | 10 |
| | ¼ | — | 20 | 30 | 0 | 30 | 30 | 30 | 0 | 0 | 10 |
| 56 | 4 | — | 80 | 90 | 50 | 70 | 100 | 100 | 20 | 20 | 10 |
| | 2 | — | 30 | 10 | 30 | — | 60 | 80 | 70 | 0 | 10 |
| 57 | 4 | — | 60 | 80 | 40 | 30 | 90 | 100 | 70 | 0 | 10 |
| | 2 | — | 70 | 40 | 0 | — | 100 | 100 | 60 | 10 | 10 |
| | 1 | — | 60 | 50 | 0 | — | 90 | 90 | 60 | 40 | 30 |
| | ½ | — | 20 | 30 | 20 | — | 90 | 100 | 50 | 10 | 20 |
| | ¼ | — | 20 | 20 | 10 | 30 | 60 | 80 | 50 | 10 | 10 |
| 58 | 4 | — | 40 | 70 | 0 | 40 | 90 | 100 | 30 | — | 20 |
| | 2 | — | 10 | 10 | 0 | — | 90 | 100 | 10 | 0 | 10 |
| | 1 | — | 50 | 50 | 30 | 20 | 70 | 100 | 30 | 20 | 30 |
| 59 | 10 | — | 0 | 10 | 0 | 0 | 0 | 80 | 0 | 0 | 0 |
| 60 | 10 | — | 80 | 60 | 10 | 70 | 90 | 100 | 30 | 10 | 10 |
| | 4 | — | 20 | 10 | 10 | 20 | 80 | 70 | 50 | 0 | 10 |
| 61 | 2 | — | 30 | 20 | 90 | 60 | 100 | 100 | 80 | 30 | 30 |
| | ½ | — | 20 | 30 | 80 | 50 | 100 | 100 | 70 | 20 | 30 |
| | ¼ | — | 60 | 60 | 90 | 70 | 90 | 100 | 40 | 20 | 30 |
| 62 | 4 | 20 | 20 | — | 0 | 20 | 100 | — | 30 | 10 | 20 |
| | 1 | 0 | 10 | — | 10 | 10 | 60 | 70 | 30 | 0 | 30 |
| | ½ | 30 | 30 | — | 0 | 10 | 70 | 50 | 10 | 0 | 20 |
| 63 | 4 | 0 | 0 | — | 0 | 0 | 90 | — | 20 | 20 | 30 |
| | 1 | 0 | 30 | — | 20 | 10 | 50 | 80 | 10 | 10 | 20 |

TABLE II-continued

| Cpd. No. | Dosage Lbs./ Acre | Post-Emergence | | | | | | | | | |
|---|---|---|---|---|---|---|---|---|---|---|
| | | CG | FM | GF | VL | CB | WM | PW | CT | CN | SB |
|    | ½ | 20 | 0 | — | 0 | 0 | 70 | 60 | 10 | 0 | 30 |
| 64 | 4 | 0 | 20 | — | 10 | 30 | 30 | 100 | 60 | 10 | 10 |
|    | 2 | 0 | 10 | — | 20 | 10 | 100 | 90 | 70 | 10 | 10 |
|    | 1 | 20 | 20 | — | 10 | 20 | 80 | 50 | 20 | 0 | 10 |
|    | ½ | 10 | 10 | — | 10 | 10 | 80 | 60 | 0 | 10 | 20 |
| 65 | 4 | 10 | 20 | — | 30 | — | 100 | 100 | 70 | 20 | 40 |
|    | 2 | — | 70 | 90 | 100 | 90 | 100 | 100 | 90 | 20 | 10 |
|    | 1 | — | 90 | 90 | 100 | 90 | 100 | 100 | 80 | 30 | 40 |
|    | ½ | — | 90 | 90 | 90 | — | 90 | 100 | 20 | 10 | 10 |
|    | ¼ | — | 50 | 40 | 70 | 70 | 90 | 100 | 80 | 30 | 40 |
| 66 | 4 | 0 | 40 | — | 10 | 20 | 90 | 100 | 20 | 40 | 30 |
|    | 1 | 0 | 0 | — | 10 | 50 | 60 | 50 | 70 | 0 | 40 |
|    | ½ | 10 | 10 | — | 20 | 40 | 40 | 50 | 10 | 0 | 40 |
| 67 | 4 | 20 | 20 | — | 10 | 60 | 40 | 100 | 50 | 40 | 50 |
|    | 2 | 10 | 10 | — | 30 | 50 | 100 | 100 | 80 | 10 | 20 |
|    | 1 | 20 | 20 | — | 0 | 10 | 20 | 100 | 20 | 10 | 40 |
|    | ½ | 20 | 0 | — | 10 | 40 | 30 | 100 | 10 | 20 | 20 |
| 68 | 10 | 20 | 20 | — | 30 | — | 100 | 100 | 90 | 20 | 50 |
|    | 4 | — | 100 | 100 | 100 | 100 | 100 | 100 | 90 | 90 | 60 |
|    | 2 | — | 100 | 90 | 100 | 100 | 100 | 100 | 80 | 60 | 90 |
|    | 1 | — | 30 | 50 | 100 | — | 90 | 100 | 90 | 20 | 30 |
|    | ½ | — | 90 | 90 | 100 | — | 90 | 100 | 90 | 70 | 90 |
|    | ¼ | — | 50 | 40 | 80 | 80 | 90 | 100 | 70 | 30 | 60 |
| 69 | 2 | — | 100 | 90 | 100 | 80 | 100 | 100 | 90 | 80 | 70 |
|    | ½ | — | 90 | 90 | 100 | 70 | 90 | 90 | 70 | 40 | 70 |
|    | ¼ | — | 50 | 40 | 100 | 60 | 90 | 90 | 90 | 50 | 60 |
| 70 | 2 | — | 90 | 80 | 100 | 70 | 100 | 100 | 90 | 70 | 60 |
|    | ½ | — | 90 | 80 | 100 | 60 | 100 | 100 | 90 | 20 | 50 |
|    | ¼ | — | 90 | 70 | 100 | 50 | 90 | 90 | 80 | 20 | 40 |
| 71 | 2 | — | 40 | 60 | 100 | 90 | 100 | 100 | 90 | 20 | 60 |
|    | ½ | — | 40 | 40 | 100 | 90 | 100 | 100 | 90 | 10 | 50 |
|    | ¼ | — | 20 | 10 | 60 | 80 | 90 | 100 | 50 | 10 | 50 |
| 72 | 10 | — | 100 | 100 | 100 | 100 | 100 | 100 | 100 | 90 | 80 |
|    | 2 | — | 100 | 100 | 100 | 90 | 100 | 100 | 100 | 80 | 80 |
|    | 1 | — | 100 | 100 | 100 | 90 | 100 | 100 | 100 | 80 | 80 |
|    | ½ | — | 90 | 90 | 90 | 90 | 100 | 100 | 90 | 50 | 80 |
|    | ¼ | — | 90 | 90 | 90 | 80 | 100 | 100 | 100 | 30 | 80 |
| 73 | 10 | — | 100 | 100 | 100 | 70 | 100 | 100 | 90 | 80 | 50 |
|    | 4 | — | 90 | 90 | 100 | 90 | 100 | 100 | 90 | 70 | 40 |
|    | 2 | — | 30 | 50 | 70 | 40 | 100 | 100 | 50 | 10 | 30 |
|    | 1 | — | 40 | 40 | 50 | 70 | 90 | 100 | 50 | 20 | 30 |
|    | ½ | — | 90 | 90 | 80 | 70 | 100 | 100 | 70 | 20 | 20 |
| 74 | 2 | — | 90 | 80 | 90 | 10 | 100 | 100 | 90 | 10 | 40 |
|    | ½ | — | 90 | 80 | 90 | — | 100 | 90 | 90 | 20 | 30 |
|    | ¼ | — | 60 | 60 | 80 | 90 | 90 | 90 | 90 | 10 | 40 |
| 75 | 2 | — | 80 | 70 | 60 | 20 | 90 | 100 | 90 | 10 | 20 |
|    | 1 | — | 90 | 80 | 80 | 40 | 100 | 70 | 70 | 20 | 20 |
|    | ½ | — | 20 | 20 | 50 | 10 | 90 | 90 | 90 | 10 | 10 |
|    | ¼ | — | 10 | 10 | 70 | — | 60 | 20 | 50 | 0 | 20 |
| 76 | 2 | — | 20 | 10 | 40 | — | 90 | 100 | 90 | 10 | 50 |
|    | ½ | — | 10 | 10 | 10 | — | 90 | 90 | 60 | 10 | 40 |
|    | ¼ | — | 10 | 10 | 80 | 30 | 80 | 70 | 40 | 10 | 10 |
| 77 | 2 | — | 90 | 90 | 100 | 90 | 100 | 100 | 50 | 20 | 30 |
|    | ½ | — | 90 | 90 | 90 | 80 | 100 | 100 | 30 | 10 | 30 |
| 78 | 10 | 60 | 20 | — | 70 | — | 100 | 100 | 90 | 70 | 30 |
|    | 4 | — | 80 | 90 | 100 | 90 | 100 | 100 | 90 | 0 | 10 |
|    | 2 | — | 100 | 100 | 100 | 90 | 100 | 100 | 90 | 50 | 70 |
|    | 1 | — | 90 | 90 | 100 | 60 | 100 | 100 | 40 | 80 | 40 |
|    | ½ | — | 90 | 90 | 90 | 80 | 90 | — | 30 | 20 | 20 |
|    | ¼ | — | 40 | 80 | 40 | 50 | 80 | 100 | 40 | 40 | 40 |
| 79 | 10 | 50 | 60 | — | 80 | — | 100 | 100 | 80 | 10 | 20 |
|    | ½ | 70 | 80 | — | 40 | 80 | 90 | 100 | 70 | 10 | 10 |
| 80 | 4 | — | 90 | 90 | 100 | 50 | 100 | 90 | 90 | 90 | 30 |
|    | 2 | — | 70 | 50 | 90 | 50 | 90 | 60 | 90 | 60 | 90 |
|    | 1 | — | 70 | 70 | 80 | 20 | 90 | 90 | 90 | 40 | 10 |
|    | ½ | — | 30 | 30 | 70 | 50 | 90 | 90 | 90 | 60 | 20 |
|    | ¼ | — | 50 | 50 | 40 | 50 | 80 | 100 | 50 | 20 | 50 |
| 81 | 2 | — | 40 | 40 | 90 | 70 | 100 | 100 | 90 | 30 | 60 |
|    | ½ | — | 30 | 30 | 100 | 50 | 100 | 100 | 90 | 10 | 40 |
|    | ¼ | — | 40 | 40 | 90 | 30 | 90 | 90 | 50 | 10 | 30 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula:

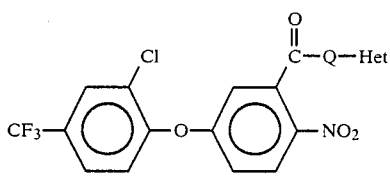

wherein Q is O or S and Het is a heterocyclic ring selected from the group consisting of s-triazinyl; 2,3-dihydro-pyridazinyl; 1,2,5-thiadiazolyl; 1,3,4-thiadiazol-5-yl; 1,2-dithio-5-21; a tetrahydro-thiophene-1,1-dioxide; 2-chloro-6-pyridinyl,1,2-dihydro-1,6-dimethyl-2-oxo-4-pyridinyl with a provision that the term Q is S when Het represents 2-pyridinyl-N-oxide.

2. A herbicidal compound as defined in claim 1, wherein Q is O.

3. A herbicidal compound as defined in claim 1, wherein Het is:

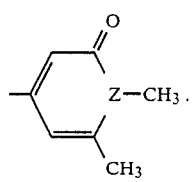

4. A herbicidal compound as defined in claim 1, wherein Het is:

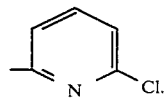

5. A herbicidal compound as defined in claim 2, wherein Het is:

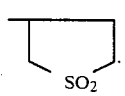

6. A herbicidal compound as defined in claim 2, wherein Het is:

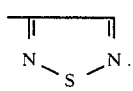

7. A herbicidal compound as defined in claim 2, wherein Het is:

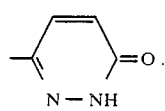

8. A herbicidal compound as defined in claim 2, wherein Het is:

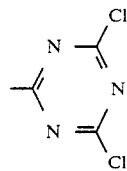

9. A herbicidal compound as defined in claim 1, wherein Q is S and Het is:

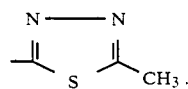

10. A herbicidal compound as defined in claim 1, wherein Q is S and Het is:

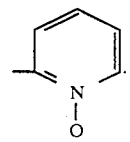

11. A herbicidal compound as defined in claim 1, wherein Q is S and Het is:

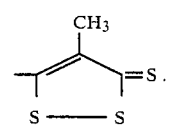

12. A herbicidal compound as defined in claim 1, wherein Q is S and Het is:

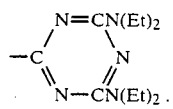

13. A herbicidal composition comprising a herbicidally effective amount of a compound according to claim 1 and a carrier therefor.

14. A herbicidal comprising a herbicidally effective amount of a compound according to claim 3 and a carrier therefor.

15. A herbicidal comprising a herbicidally effective amount of a compound according to claim 5 and a carrier therefor.

16. A method for combatting undesirable herbs which comprises contacting them with a herbicidally effective amount of a compound according to claim 1.

17. A herbicidal composition comprising a herbicidally effective amount of a compound according to claim 4 and a carrier therefore.

18. A method for combatting undesirable herbs which comprises contacting them with a herbicidally effective amount of a compound according to claim 4.

19. A method for combatting undesirable herbs which comprises contacting them with a herbicidally effective amount of a compound according to claim 3.

20. A method for combatting undesirable herbs which comprises contacting them with a herbicidally effective amount of a compound according to claim 5.

* * * * *